(12) United States Patent
Priori et al.

(10) Patent No.: US 7,741,529 B1
(45) Date of Patent: Jun. 22, 2010

(54) TRANSGENIC ANIMAL MODEL FOR CATECHOLAMINERGIC POLYMORPHIC VENTRICULAR TACHYCARDIA (CPVT) AND USE THEREOF

(76) Inventors: Silvia G. Priori, Via Londonio, 1, Milano (IT) 20154; Carlo Napolitano, Corso Sempione, 11, Milano (IT) 20145

( * ) Notice: Subject to any disclaimer, the term of this patent is extended or adjusted under 35 U.S.C. 154(b) by 0 days.

(21) Appl. No.: 11/429,167

(22) Filed: May 4, 2006

(51) Int. Cl.
*A01K 67/027* (2006.01)
*A01K 67/00* (2006.01)
*G01N 33/00* (2006.01)
*C12N 15/63* (2006.01)

(52) U.S. Cl. .............................. 800/18; 800/3; 800/13; 800/14; 435/320.1

(58) Field of Classification Search ...................... None
See application file for complete search history.

(56) References Cited

U.S. PATENT DOCUMENTS 5,464,764 A * 11/1995 Capecchi et al. ............... 435/6
2007/0254849 A1 * 11/2007 Chen et al. ..................... 514/35

OTHER PUBLICATIONS

Alting-Mees et al. Nucleic Acids Res. Nov. 25, 1989; 17(22): 9494.*
Kappell et al (1992) Current Opinion in Biotechnology 3: 548-553.*
Mullins et al (1993) Hypertension 22: 630-633.*
Houdebine (1994) J. Biotech. 34: 269-287.*
Wall (1996) Theriogenology 45: 57-68.*
Mullins et al. Journal of Clinical Investigation, 1996. vol. 97, No. 7: 1557-1560.*
Cameron (1997) Molec. Biotechnology. 7: 253-265.*
Sigmund (2000) Arteroscler. Throm. Vasc. Biol. 20: 1425-1429.*
Niemann (1998) Transgenic Research. 7: 73-75.*
Moreadith et al., J. Mol. Med., 1997. 75:208-216.*
Pera et al. Journal of Cell Science. 2000.113: 5-10.*
Cerrone et al. (Circ. Res. 2005; 96: 77-82).*
Kuzmanovic et al. (IOVC. Aug. 2003; 44(8): 3606-3613).*
Ahern et al., "Effects of Ivermectin and Midecamycin on Ryanodine Receptors and the $Ca^{2+}$-ATPase in Sarcoplasmic Reticulum of Rabbit and Rat Skeletal Muscle," The Journal of Physiology 514:313-326, 1999.
Benkusky et al., "Ryanodine Receptor Channelopathies," Biochemical and Biophysical Research Communications 322:1280-1285, 2004.
Cerrone et al., "Bidirectional Ventricular Tachycardia and Fibrillation Elicited in a Knock-In Mouse Model Carrier of a Mutation in the Cardiac Ryanodine Receptor," Circulation Research 96:e77-82, 2005.
Colomo et al., "Active and Passive Forces of Isolated Myofibrils from Cardiac and Fast Skeletal Muscle of the Frog," Journal of Physiology 500(pt 2):535-548, 1997.
El-Hayek et al., "Altered E-C Coupling in Triads Isolated from Malignant Hyperthermia-Susceptible Porcine Muscle," American Journal of Physiology 268:C1381-C1386, 1995.

George et al., "Ryanodine Receptor Mutations Associated With Stress-Induced Ventricular Tachycardia Mediate Increased Calcium Release in Stimulated Cardiomyocytes," Circulation Research 93:531-540, 2003.
Györke et al., "Regulation of the Cardiac Ryanodine Receptor Channel by Luminal $Ca^{2+}$ Involves Luminal $Ca^{2+}$ Sensing Sites," Biophysical Journal 75:2801-2810, 1998.
Harkins et al., "Resting Myoplasmic Free Calcium in Frog Skeletal Muscle Fibers Estimated with Fluo-3," Biophysical Journal 65:865-881, 1993.
Jiang et al., "Enhanced Basal Activity of a Cardiac $Ca^{2+}$ Release Channel (Ryanodine Receptor) Mutant Associated with Ventricular Tachycardia and Sudden Death," Circulation Research 91:218-225, 2002.
Jiang et al., "RyR2 Mutations Linked to Ventricular Tachycardia and Sudden Death Reduce the Threshold for Store-Overload-Induced $Ca^{2+}$ Release (SOICR)" Proceedings of the National Academy of Sciences, U.S.A. 101:13062-13067, 2004.
Karreman, "New Positive/Negative Selectable Markers for Mammalian Cells on the Basis of Blasticidin Deaminase-Thymidine Kinase Fusions," Nucleic Acids Research 26:2508-2510, 1998.
Laitinen et al., "Mutations of the Cardiac Ryanodine Receptor (RyR2) Gene in Familial Polymorphic Ventricular Tachycardia," Circulation 103:485-490, 2001.
Lande et al., "Transgenic Mice Overexpressing Human KvLQT1 Dominant-Negative Isoform Part II: Pharmacological Profile," Cardiovascular Research 50:328-334, 2001.
Leenhardt et al., "Congenital Heart Disease: Catecholaminergic Polymorphic Ventricular Tachycardia in Children: A 7-Year Follow-up of 21 Patients," Circulation 91:1512-1519, 1995.
Priori et al., "Clinical and Molecular Characterization of Patients with Catecholaminergic Polymorphic Ventricular Tachycardia," Circulation 106:69-74, 2002.
Priori, "Inherited Arrhythmogenic Diseases: The Complexity Beyond Monogenic Disorders," Circulation Research 94:140-145, 2004.
Priori et al., "Mutations in the Cardiac Ryanodine Receptor Gene (hRyR2) Underlie Catecholaminergic Polymorphic Ventricular Tachycardia," Circulation 103:196-200, 2001.
Rodriguez et al., "High-efficiency Deleter Mice Show that FLPe is an Alternative to Cre-*loxP*," Nature Genetics 25:139-140, 2000.
Sambrano et al., "Navigating the Signalling Network in Mouse Cardiac Myocytes," Nature 420:712-714, 2002.

(Continued)

*Primary Examiner*—Scott Long
(74) *Attorney, Agent, or Firm*—Clark & Elbing LLP

(57) ABSTRACT

The present invention refers to non-human transgenic mammals, preferably rodents, or mice, which comprise a mutation in the gene encoding for the cardiac ryanodine receptor (RyR2).

Transgenic animals carrying the amino acid change R4496C in the RyR2 protein show a phenotype similar to that of Catecholaminergic Polymorphic Ventricular Tachycardia (CPVT) (OMIM: 604772). Further provided are methods for using these animals as in vivo model of Catecholaminergic Polymorphic Ventricular Tachycardia and RyR2 dependent arrhythmias, in drug screening and for understanding the molecular basis of RyR2 dependent arrhythmias.

20 Claims, 6 Drawing Sheets

OTHER PUBLICATIONS

Sambrook et al., *Molecular Cloning a Laboratory Manual, Second Edition*. Cold Spring Harbor Laboratory Press, 1989.

Swan et al., "Arrhythmic Disorder Mapped to Chromosome 1q42-q43 Causes Malignant Polymorphic Ventricular Tachycardia in Structurally Normal Hearts," Journal of American College of Cardiology 34:2035-2042, 1999.

Tesi et al., "Modulation by Substrate Concentration of Maximal Shortening Velocity and Isometric Force in Single Myofibrils from Frog and Rabbit Fast Skeletal Muscle," The Journal of Physiology 516(pt 3):847-853, 1999.

Tournier et al., "Analysis of the Allele-Specific Expression of the Mismatch Repair Gene MLH1 Using a Simple DHPLC-Based Method," Human Mutation 23:379-384, 2004.

Viatchenko-Karpinski et al., "Abnormal Calcium Signaling and Sudden Cardiac Death Associated With Mutation of Calsequestrin," Circulation Research 94:1-7, 2004.

Volinia et al., "GOAL: Automated Gene Ontology Analysis of Expression Profiles," Nucleic Acids Research 32:W492-W499, 2004.

Wehrens et al., "FKBP12.6 Deficiency and Defective Calcium Release Channel (Ryanodine Receptor) Function Linked to Exercise-Induced Sudden Cardiac Death," Cell 113:829-840, 2003.

Zahradnikova et al., "Rapid Activation of the Cardiac Ryanodine Receptor by Submillisecond Calcium Stimuli," The Journal of General Physiology 114:787-798, 1999.

Cerrone et al., "Bidirectional Ventricular Tachycardia and Fibrillation Elicited in a Knock-In Mouse Model Carrier of a Mutation in the Cardiac Ryanodine Receptor," Circ. Res. 96:E77-E82, 2005.

Babji et al., "Inhibition of Cardiac Delayed Rectifier K+ Current by Overexpression of the Long-QT Syndrome HERG G628S Mutation in Transgenic Mice," Circ. Res. 83:668-678, 1998.

Napolitano, "Transgenic Models in Cardiac Arrhythmias: How Close Can We Get to the Bedside?" Cardiovasc. Res. 61:206-207, 2004.

Nerbonne et al., "Genetic Manipulation of Cardiac K+ Channel Function in Mice," Circ. Res. 89:944-956, 2001.

Babji et al., "Inhibition of Cardiac Delayed Rectifier K+ Current by Overexpression of the Long-QT Syndrome HERG G628S Mutation in Transgenic Mice," Circ. Res. 83:668-678, 1998.

Cerrone et al., "Arrhythmogenic Mechanisms in a Mouse Model of Catecholaminergic Polymorphic Ventricular Tachycardia," Circ. Res. 101:1039-1048, 2007.

Chen et al., "KCNQ1 Gain-of-Function Mutation in Familial Atrial Fibrillation," Science 299:251-254, 2003.

Kannankeril et al., "Mice with the R176Q Cardiac Ryanodine Receptor Mutation Exhibit Catecholamine-Induced Ventricular Tachycardia and Cardiomyopathy," Proc. Natl. Acad. Sci. USA 103:12179-12184, 2006.

Yang et al., "Human KCNQ1 S140G Mutation is Associated with Atrioventricular Blocks," Heart Rhythm 4:611-618, 2007.

* cited by examiner

SEQUENCE LISTING

<160> NUMBER OF SEQ ID NOS: 6

<210> SEQ ID NO 1
<211> LENGTH: 2504
<212> TYPE: DNA
<213> ORGANISM: Mus musculus
<220> FEATURE:
<221> NAME/KEY: Intron
<222> LOCATION: (1)..(2504)
<223> OTHER INFORMATION: RyR2 intronic region: Ex. 93-Ex. 94.
      Partial

<400> SEQUENCE: 1

```
ctagattatt tacaatctca aatgcagtat gaatgttgtg gaaacgtata atatagtgaa      60
tcatttaggg aataatggta agagaaaaaa gtctatatcc atttaggaca aaatgttgtc     120
taagtatttt ctctttgcaa ctgatttgac ctataaaggc tcaagttgtt tgacctacga     180
gagctaagca gatgttcatc tactcattta gtgatttgga tttttgaaac agttgatctt     240
tattttatat gtacatgtga atgtttccat gcgttgatgt attccatgag tatgcaagtg     300
cctgaggggg ccagaagagg gcatctgata ccctggatct gaagttacag acatttgtga     360
gctatcatgt gggtgctggg aaccaaacct aggtccoctg cactggcagc cagtgctctt     420
aattttttgag ccatctttac aacccagtgt atttgtgttt taaagcaaat gtcttttttct    480
caagctactg ctccttctac aatatttata ctgcctgata ctctgtggcc tctacacacc     540
ttcacatggt ctgatgcccc caaggcctct atatgtgtta ctgtcttgac atccctcaac     600
tgaataacca cagtagtcca tagtcttcca acatatactt tagaacccat caggcatatt     660
ttcaaggctc tgtaatagtt gaccataaac taggcatagc ctccttggtc catggaattt     720
atagttcagc ccagaaccaa atgagtctat catcccacct tttatttaaa agaaatatgt     780
ataaatgtat agaagtaaaa cataaatata ttttataagt ataaacctaa tgagtcagct     840
tttcagtgac gataattcaa aaattttctt tagagacaag taaaagaaag tgaaatgaga     900
aaaagaagat agttcttcat agggttttct aggagtattt ccaaatcttg tgttttctct     960
atattgtttg agtccattga acataacgtt ttctgagaca actctgtgta actgttaatt    1020
tgatatgcat cagtggttgc tatagcagca ggcatctctt tgtagatgct ttggaggttg    1080
ggtaggctct tcagtaacct ctagcagctc tgtggttccc aagagcctgt ctctgtagtt    1140
gcttaaggaa agcaactgag gctgtccttt cttttctgcc tctccgttcc tatgtttccc    1200
aattttatgt aactcttcca ccgctctcca tcttttttgta gcttaggcat tggcttgcca    1260
gtttgcattc atcagaccaa tgatggccat gatgcttgcc ccctgcccat agatctctct    1320
tttccatgtc tttgtgacag tcccatacaa aagccatagt tagataactc catctctgtg    1380
acctattttg ttactttcta ggagataata ccaatataat tggcccaatt tgagtatgtc    1440
attcagtcct agtacaacta ggtgtggcag taaagccagc attcactgta gggcggagac    1500
cccaaagagg gggtgagtcc acggagagat tagtgagagg cattgctatg gttaggcatt    1560
atcaggctaa agctcagttc atgttataac aaacagtagc ttccaatgta gcctcttccc    1620
ttacatcctc ttctgctgag ttgctttggc ttcctctgat tcaatgtgcc atactaacca    1680
gtcacttagt gctgatcttt gagtcctttc tctcttactt ctgtcttact tctcttactt    1740
tctctcttac tttctagaac agaaaacaaa cagcaaccct cagttcttct ttcaaagttc    1800
ctcaaaggtc tacctagttc catgtccaca gctacaatgg aagcaaaccc gctgacaaca    1860
```

-continued

```
tcacctctttt ttgtggccat gcctactaac ctgttttctt tatttcttca atagcatctt    1920
atccacacta gagtaaaaca gcaattataa cagtggcagc atacaaagta tcatatatta    1980
ctactagtag catattaaaa tgaataacgg atttctcgta tattctcaat aattctcgta    2040
gcaagtataa gaggctggtt ctgttgttat gttcacacta cagaagagac aagatatgtt    2100
ctaggaagaa ttaggtcatt catccacatt ttgaatccag gaaatgcgag gacagacttc    2160
acatgtgtaa agtgtagtct tgggggtcgt aagtggatttt agagatcatt gaatcagttt    2220
actgtaatgg acaactcaaa tctttatcag gggcctttaa aactcagctc ctgcacacac    2280
acacacatac acacacacac acacacacac acacacacat acacacacat cccattattc    2340
tttattaata cttctggagg ctagatgagg gcatcagatc cccctaagtt agagttatag    2400
gtagttgtga acttctgtgt gtgctggaaa ctgaacccag atcttctgca agaacagcac    2460
atgtgcttaa ccctctctat agccccactc gttacttcag ggcc                     2504
```

<210> SEQ ID NO 2
<211> LENGTH: 614
<212> TYPE: DNA
<213> ORGANISM: Mus musculus
<220> FEATURE:
<221> NAME/KEY: misc_feature
<222> LOCATION: (1)..(614)
<223> OTHER INFORMATION: exon 94 carrying the C to T mutation in codon
      corresponding to nt 387-389

<400> SEQUENCE: 2

```
ccgttggcac tatccatgtc tctaaaacac cttcccctg tgttggctca ggtagctccc       60
ttgccatccc caggcctgtg ctccagctca cctcctgaca taagccttc ctaaccacct      120 attccaaatt atcatctcac tccctaaacc ctcacctatg tatcaatatg ccttttagag     180
tccttgaatg atatgtaaag gtgtggttat tgttagttct cactttgtcc tttgctgtgt    240
gtctctagca ccaagaccac aataggctct caatctgtat agtctggagt aaatgaatga    300
atgccttgtt taaaacgttt gcccatctcc gatctcttac ctagtggcct attcttaatt    360
ctttctctct tcagaactat tttgcttgca acttttacaa catgagaatg ctggccttgt    420
ttgttgcctt cgccatcaat ttcatcctgc tcttctacaa ggtatgtacg tgtgttttgg    480
tgagttaaag accgttctga atgtgaaaag tgactgatgc caatggatag attccccatg    540
aactgcgatt catattacta caccaattct aaactgcatc ttaaccaaga gacaggccaa    600
agcccaggcc tcct                                                       614
```

<210> SEQ ID NO 3
<211> LENGTH: 924
<212> TYPE: DNA
<213> ORGANISM: Mus musculus
<220> FEATURE:
<221> NAME/KEY: Intron
<222> LOCATION: (1)..(924)
<223> OTHER INFORMATION: Exon 95 and flanking regions

<400> SEQUENCE: 3

```
gatgccccag aagacggtgc ctgcactcct ggcaagtgag ggggaggaac atcagctggc      60
caggactgag agggtcgagt gttacagagg gttcaccca gtgttcctag gacgattcag      120
ttgaatttct tacttgttat gatttacgat gactggatga gacagaccct ttctcacatg    180
acattatatg gataactgag aagaaaagta tctagtactt tctgtacaat ttgggatcct    240
tataactttt tgttggatta gcatgaactt taaaaagatt aactgtgtgt gtgaggcagc    300
```

```
aagtgctttt tctgactaag ttctctctca gcaaccccca gccccagcat aaactttaga    360
cacatactta ttacatgagt tttctgttgg aaaagctgtc tctttacgat ttcctcatag    420
tctttccatg ataccattat gtactggctt catacccaac tgtctgcaga tatcatgttt    480
tcatttcttt ctgtttatga cgacgtggca tgcagagaac tgactgtatt ttaaatggtt    540
tgaatcaggt ctccacttct tctgtggttg aaggaaagga gctgcctacc cgaacctcca    600
gcgatactgc taaagtgacc aacagcctag acagcagccc ccacaggatc attgcggttc    660
actatgtcct ggaggagagc agcggctaca tggaacccac cctgcgcatc ttagccatcc    720
tccacaccat catctccttc ttttgcatca tcggatacta ctgcttgaaa gtaagtcccc    780
aggtatctgt gcgtgtagag tgcctgtctg tactgtggac ttctggggat tctggtgctg    840
aggggggatt tccaagtgtg gcattttatt taggatgctc tagggatcca cacctctggg    900
gcagaagggg taagcaggtt ggag                                            924
```

```
<210> SEQ ID NO 4
<211> LENGTH: 23
<212> TYPE: DNA
<213> ORGANISM: artificial
<220> FEATURE:
<223> OTHER INFORMATION: primer
<220> FEATURE:
<221> NAME/KEY: primer_bind
<222> LOCATION: (1)..(23)

<400> SEQUENCE: 4
cacatcgcta tggggagccg aag                                             23

<210> SEQ ID NO 5
<211> LENGTH: 23
<212> TYPE: DNA
<213> ORGANISM: artificial
<220> FEATURE:
<223> OTHER INFORMATION: primer
<220> FEATURE:
<221> NAME/KEY: primer_bind
<222> LOCATION: (1)..(23)

<400> SEQUENCE: 5
cgaaggcaac aaacaaggcc agc                                             23

<210> SEQ ID NO 6
<211> LENGTH: 26
<212> TYPE: DNA
<213> ORGANISM: artificial
<220> FEATURE:
<223> OTHER INFORMATION: primer
<220> FEATURE:
<221> NAME/KEY: primer_bind
<222> LOCATION: (1)..(26)

<400> SEQUENCE: 6
cagcattctc atgttgtaaa agttgc                                          26
```

US 7,741,529 B1

TRANSGENIC ANIMAL MODEL FOR CATECHOLAMINERGIC POLYMORPHIC VENTRICULAR TACHYCARDIA (CPVT) AND USE THEREOF

BACKGROUND OF THE INVENTION

Catecholaminergic polymorphic ventricular tachycardia (CPVT; OMIM: 604772) is a highly malignant cardiac disease manifesting in childhood and adolescence. It is characterised by adrenergically-mediated bidirectional or polymorphic ventricular tachycardia leading to syncope and/or sudden cardiac death[1, 2]. Based on previously reported linkage data that had mapped the disease to chromosome 1q42-43[3], we reported that the gene for the autosomal dominant variant of CPVT was RyR2; i.e. the gene encoding for the cardiac isoform of the ryanodine receptor[4]. The first family in which a RyR2 mutation was identified was affected by a highly malignant form of the disease that was resistant to beta-blockers; the mutation present in the family (R4497C) is a hot spot that we subsequently identified in other CPVT patients unrelated to the first kindred. The R4497C mutation has been extensively investigated in different in vitro models that demonstrated that it causes abnormal release of calcium from the sarcoplasmic reticulum[5-8]. It has been therefore inferred that arrhythmias may develop as a consequence of this defect of intracellular calcium handling. However, experimental evidence linking this mutation to the development of life threatening arrhythmias is still lacking. The cardiac ryanodine receptor (RyR2) is a large tetrameric intracellular calcium ($Ca^{2+}$) release channel located in the sarcoplasmic reticulum (SR) that has a pivotal role in excitation-contraction coupling. In response to a small intracellular $Ca^{2+}$ influx through the L-type voltage dependent $Ca^{2+}$ channels, RyR2 releases from the SR the large amount of $Ca^{2+}$ that is needed to elicit contraction of the cardiac cell. However, in addition to such a tightly regulated physiological process, RyR2 may also release $Ca^{2+}$ in response to SR and luminal calcium overload, which may occur under pathological conditions such as physical and emotional stress, digitalis toxicity and heart failure. In such instances RyR2 may become a crucial player for the development of life-threatening arrhythmias.

Previously, we reported that mutations in the gene encoding for RyR2 cause the autosomal dominant form of catecholaminergic polymorphic ventricular tachycardia (CPVT)[4]. Shortly after, other groups confirmed this finding and reported novel RyR2 mutations in patients affected by CPVT[9]. More than 20 RyR2 mutations have been reported in the literature[10].

The first mutation that we identified in an Italian CPVT family leads to the replacement of arginine at position 4497 with a cysteine. Since this mutation was associated with a very typical CPVT phenotype it has been selected by several authors for their in vitro studies aimed at the functional characterization of RyR2 mutants. Jiang, D. et al., in[6] were the first to investigate the R4496C mouse equivalent of the R4497C human mutation. They suggested that when expressed in HEK293 cells the mutation enhances the basal channel activity and the propensity for spontaneous calcium release at rest and in response to caffeine. More recently, the same authors further elaborated their results and proposed that the R44967C (or its murine homolog R4496C), as well as other RyR2 mutations identified in CPVT families, increase the sensitivity of RyR2 channels to luminal [$Ca^{2+}$] thus facilitating the spontaneous release of $Ca^{2+}$ from the SR[5]. George et al[7] investigated the same mutation by expression in HL-1 cardiac myocytes. At variance with what was suggested by Jiang et at[5] based on their studies in HEK 293 cells, George et al.[7] reported that the R4496C mutant presents no enhancement of basal activity but they confirmed that after exposure to the RyR agonist caffeine or to beta adrenergic stimulation, calcium release was significantly augmented in the mutant channels. George et al also showed that the dissociation of the FKBP12.6 protein from the mutant was similar to that observed in the WT RyR2 thus challenging the hypothesis advanced by Wehrens et al[8] who proposed that the enhanced calcium release observed in the mutant during beta adrenergic stimulation was caused by the excessive dissociation of the RyR2:FKBP12.6 complex. Overall, although disagreement exists on the mechanisms by which the R4496C mutation sensitizes the RyR2 channel to agonists, three independent groups have confirmed that upon caffeine and beta adrenergic stimulation RyR2$^{R4496C}$ channels respond with an augmented calcium release.

The large amount of data reported in the last few years suggest that RyR2-R4497C (or its murine homolog R4496C) is a kind of prototype among RyR2 mutation very suitable to study the mechanisms cardiac arrhythmias due to intracellular $Ca^{2+}$ handling abnormalities.

Here we report on a conditional knock-in mouse model carrier of the R4496C mutation that is the mouse equivalent of the human mutation R4497C. The aim of the present work is to generate an animal model of CPVT allowing to better characterize the clinical phenotype, the pathogenetic mechanisms and to gather insights on possible novel therapies of CPVT and RyR2-mediated arrhythmogenesis in general.

SUMMARY OF THE INVENTION

The present invention refers to non-human transgenic mammals, preferably rodents, or mice, which comprise a mutation in the gene encoding for the cardiac ryanodine receptor 2 (RyR2).

Transgenic animals carrying the amino acid change R4496C in the RyR2 protein show a phenotype similar to those of Catecholaminergic Polymorphic Ventricular Tachycardia (CPVT) (OMIM: 604772). CPVT is a highly malignant cardiac disease in humans, manifesting in childhood and adolescence, leading to syncope and/or sudden cardiac death and which is often linked to mutation in the RyR2 sequence.

Accordingly, the heart of animals carrying such a mutation is predisposed to Ventricular Tachycardia (VT) and Ventricular Fibrillation (VF) in response caffeine and/or adrenergic stimulation and/or physical stress.

In one embodiment the present invention provides a vector for targeting of the RyR2 gene, in particular the region encompassing exon 94. The vector carries a mutated exon 94, at nucleotide n° 13486 of the coding RyR2 sequence (GenBank cDNA entry: NM_023868, genomic entries: NT_039576 and NW_001030510), which determines the point mutation C→T in the codon corresponding to nt 387-389 of seq IDNO2 and the amino acidic change R4496C. The region encompassing exon 94 in the targeting vector corresponds to seqIDNO2. A schematic representation of a preferred embodiment of the vector is depicted in FIG. 1.

Mutated exon 94 and surrounding intronic regions are flanked by recombination sites, preferably Lox-P or FRT sites, in the vector of the present invention. At least one selectable marker, linked to a promoter and preferably flanked by recombination sites, i.e. FRT sequences, is comprised in the vector. According to a preferred embodiment of the invention, at least one positive and one negative selection marker are carried by the vector. Additional genomic fragments flanking exons 94 are present at the 5' and 3' end of this construct to allow homologous recombination.

According to a further embodiment the invention provides a cell isolated from the RyR2 R4496C mutant transgenic mouse. The cell is preferably a muscle cell, more preferably a cardiac muscle cell. A further embodiment is represented by in vitro methods where such cells are used in drug screening and for functional assays.

According to a further embodiment, the invention provides a method for screening compounds by using the transgenic model of the invention. The therapeutic effect of potential drug candidates, in treating or preventing arrhythmias in the transgenic animal, preferably in rodents, is measured by electrocardiographic analyses, microeletrode recordings in myocardial tissue, single cell experiments (voltage-clamp or current-clamp modes). Measures are taken after or just before induction of stress conditions such as exercise stress, optionally in combination with administration of molecules able to alter the $Ca^{2+}$-fluxes, such as caffeine or its analogues and/or of beta-adrenergic compounds and by comparing the responses of transgenic mice to the ones of wild type animals or of suitable controls (untreated wild type and/or transgenic animals). Furthermore the transgenic animals of the invention are used as a gene therapy model for RyR2 mediated arrhythmias in vivo or in vitro treatment by viral vectors or antisense technology (siRNA).

The transgenic mice of the invention are useful in crossbreeding experiments with mice harbouring abnormalities in other proteins controlling intracellular calcium handling in order to gather further pathophysiological insights.

DESCRIPTION OF THE PREFERRED EMBODIMENTS

The present invention refers to a non-human transgenic mammal, preferably a rodent, even more preferably a mouse, which comprises a mutation in the gene encoding for the cardiac isoform of ryanodine receptor (RyR2). Transgenic animals show a phenotype similar to those of Catecholaminergic polymorphic ventricular tachycardia (CPVT) (OMIM: 604772). CPVT is a highly malignant cardiac disease in humans, manifesting in childhood and adolescence, leading to syncope and/or sudden cardiac death and which is often linked to mutation in the RyR2 sequence.

Mice

Although any small-sized mutant RyR2 transgenic mammals represent a useful model for cardiac anomalies or arrhythmias, rodents are preferred, particularly mice (*Mus muris*). Any murine species can be used for the preparation of the RyR2 transgenic mouse. The most commonly used for experimental work are the following: Balb/J, SWR/J, CBA/J, C57L/J, CH3/HeJ, C57Bl/6J, CH3Heb/FeJ, AKR/, DBA/2J, A/J. According to a preferred embodiment the RyR2 transgenic mouse is a chimera between C57Bl and 129SV genotypes. Integration of the transgene in the cells, tissues or animals is confirmed by molecular methods, such as those described in[11] or i.e. by PCR or Southern-blot on purified nucleic acids isolated from tissue biopsy specimen (i.e. tail).

Mutated Gene and Vector

A mutated exon of the RyR2 gene, or an exonic fragment, is prepared according to molecular methods such as those described in[11]. According to a preferred embodiment, a C→T mutation is introduced in the codon corresponding to nt 387-389 of seq IDNO2 (encompassing exon 94) by subcloning this fragment into a cloning vector such as pBlueScript. This mutation brings to the amino acidic change from arginine to cysteine (R4496C) in the murine RyR2 protein. This mutation corresponds by homology comparison and alignment analysis to the human RyR2 R4497C mutation. GenBank acc. N° of the murine sequences: cDNA, NM_023868; genomic NT_039576 and NW_001030510.

For the preparation of transgenic mouse any targeting vector can be used: in a preferred embodiment the vector is a replacement vector such as the vector pFRT (see Gene Bank entry AY268481).

Figure 1:
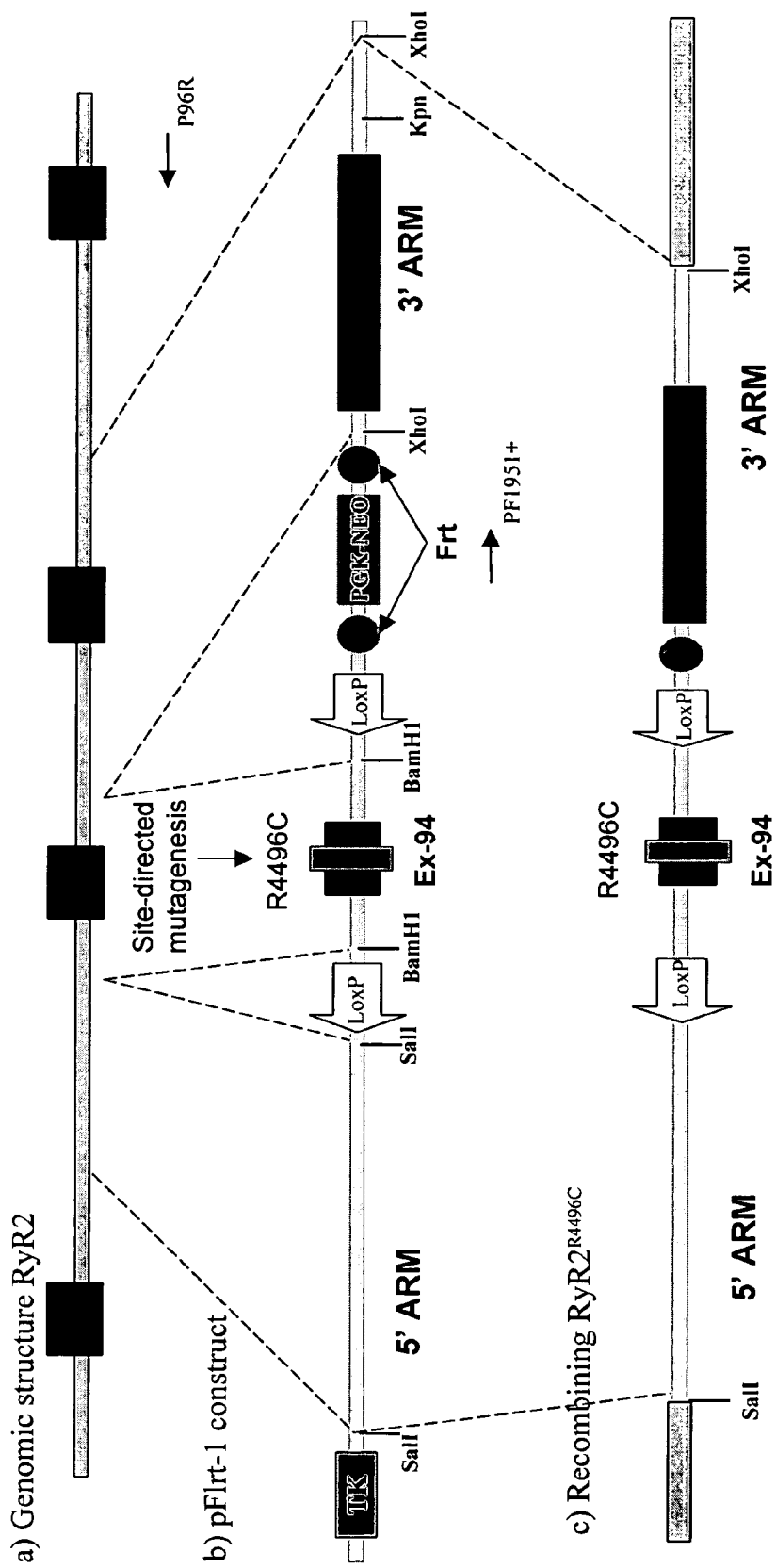
FIG. 1. Schematic representation of the genomic structure of mouse RyR2 (a); the targeting vector used to generate the knock-in $RyR^{R4496C}$ mouse strain (b); the recombining genomic structure of $RyR^{R4496C}$(c). Ex=exon.

Genomic regions as arms of homology for homologous recombination into the mouse genome, are present at the 5' and 3' of a "replacement cassette" (see FIG. 1). A particularly preferred 5' arm is seqIDN1 and a particularly preferred 3' arm is seqIDN3.

The "replacement cassette" comprises:
  a mutated exon 94 as described above, flanked by recombinase sites. As Cre recombinase sites any Lox site or its operational mutants can be used. Other recombination sites such as FIp recombinase sites can be used, i.e. the FRT 34 bp consensus or mutants thereof[12];
  at least a selection marker, operably linked to a promoter. The selection marker/s is/are preferably flanked by recombinase sites as described above. Selection markers may be a positive or a negative. Among positive selectable markers: the neo gene (neomycin phosphotransferase G418) or its mutants; the puromycin resistance gene (puro); the hygromycin resistance gene (hygro);

the hypoxanthine phosphoribosyl transferase (hprt) which can be used also as a negative selectable marker if the starting cell is hprt deficient.

In a preferred embodiment the vector comprises both positive and negative selection markers, for example a Neo resistance gene as a positive selection marker and thymidine kinase (TK) gene from herpes simplex virus (HSV) as a negative selection marker when used with Gancyclovir™[13]. Particularly preferred in the present vector are the Neo and TK gene for G-418™ (positive) and Gancyclovir™ (negative) selection, respectively. The vector may optionally comprise reporter genes, such as GFP, LacZ or alkaline phosphatase.

Other genomic elements for the regulation, expression, stabilization of the transgene or of other vector genetic elements, i.e. promoters, enhancers, TATA-box, IRES can optionally be present.

Methods for the Preparation of Transgenic Animals

Transgenic animals, preferably mice, are prepared according to methods known in the art. The method is preferably Embryonic Stem (ES) cell mediated. Several murine Embryonic Stem cell lines can be used, such as CB1-4 ES, CCE, 129/Ola: particularly preferred are TVB2 ES, isolated from 129SV/J mice. ES transformation is carried out with the vector according to the invention, linearized, purified and electroporated into ES cells. Other transfection methods may be used, such as microinjection. ES selection is performed in a culture medium comprising the selective agent/s at a suitable concentration. Other cloning and manipulation methods are described in Manipulating the Mouse Embryo: a laboratory manual $2^{nd}$ ed. CSH 1994. Particularly preferred is the combination of 129SV/J ES in a C57Bl/6J blastocyst.

Selected transgenic ES cells are transferred into a compatible blastocyst to obtain chimeric animals and are introduced into foster mother. The resulting chimeric animals are bred to wild type animals to establish hybrid F1. Some of the chimeric animals will harbour the transgenic in the germinal cells and will transmit it to the offspring. Thus, by mean of PCR genotyping and Southern blotting on DNA extracted from tail specimen of F1 it is possible to identify those animals that have received the mutation (and may transmit it to the offspring). According to a preferred embodiment the resistance gene, when flanked by recombination sites, can be excised by breeding transgenic animals with recombinase transgenic animals.

RyR2 Mutations

Various mutations in the RyR2 receptor are known[10]. The R4497C RyR2 mutation in humans leads to CPVT and/or to sudden death and it is considered a sort of prototype of RyR2 genetic defect. From a clinical standpoint RyR2-R4497C is the first RyR2 identified mutation in a family in which it was associated with complete penetrance. Other mutation carriers have been identified afterwards and all show the typical CPVT manifestations with exercise/emotion-induced bidirectional and polymorphic ventricular tachycardia (FIG. 3 panel A), high incidence of sudden death among untreated subjects, incomplete response to beta blocker therapy[2]. The murine RyR2 mutation R4496C corresponds to the human mutation R4497C by amino acid homology comparison (mouse cDNA NM_023868; human cDNA NM_001035)

Cardiac Activity Measurement and Definitions of Cardiac Abnormalities

The cardiac activity in transgenic animals is preferably measured by continuous ECG monitoring. ECG radiotelemetry monitors (Data Sciences International) are typically implanted intraabdominally under general anaesthesia. After recovery from surgery the electrocardiographic signal is recorded continuously in conscious animal kept in special cages provided with receivers and connected to a A/D converted an a PC for data storage. Off-line analyses of stored ECGs parameters comprise: quantification of arrhythmias, heart rate trends, heart rate variability assessment (power spectrum analysis), QT interval and T wave assessments. Other parameters of cardiac functionality measurable by ECG are the following: baseline QT interval (measured using the tangent method[23]), RR interval, RR variability.

Arrhythmias in transgenic mice is defined as follows: non sustained ventricular tachycardia (VTns) is a series of 4 to 10 consecutive repetitive ventricular ectopic beats (VEBs), sustained VT (VTsust) is a run of >10 consecutive VEBs, ventricular fibrillation (VF) is a VTsust degenerating into ventricular fibrillation leading to sudden death. Ventricular tachycardia in the mutant RyR2 transgenic mouse closely resembles the human CPVT (FIG. 3 panel B)[14].

Induction of arrhythmias in the mouse model is usually obtained by exercise on a treadmill until exhaustion followed by injection of epinephrine (2 mg/kg i.p.) or by injection of epinephrine (2 mg/kg i.p.) and caffeine (120 mg/kg i.p.) without exercise.

Measures of cardiac excitability can be carried out in combination with a different technique, i.e. together with a morphologic evaluation of the heart, performed by echocardiograms or Nuclear Magnetic Resonance (NMR), or with measurement of the blood pressure.

Isolated Cells and Methods of Use Thereof

The invention further provides a cell isolated from the R4496C transgenic rodent or mouse according to the invention. The cell is preferably a muscle cell, more preferably a cardiomyocyte. Methods for isolating and culturing cardiac cells are described for example in[15].

A preferred use of such cells is for testing a candidate compound (test compound) for any antiarrhythmic activity.

Another use of isolated mutated RyR2 cells is in in vitro assays aimed at the understanding of the molecular and electrophysiological basis of arrhythmias. This is achieved starting from the identification of the cellular players able to modulate RyR2 expression levels or function, for example those acting on the intracellular $Ca^{2+}$ handling (i.e. $Ca^{2+}$ antagonists, modulators of RyR2 interacting molecules, such as calstabin, inhibitors of the $Na^+/K^+$ pump and $Na^+/Ca^{2+}$ exchanger), blockers of the delayed sodium current $I_{sus}$) in mutant RyR2 cells and/or in wild type cells.

RyR2 function as $Ca^{2+}$ channel is measured by $Ca^{2+}$ flux on a single cell isolated from transgenic mice as described e.g. in[16]. Typically, a fluorescent ion indicator such as Calcium Green, Fluo-3, Fluo-4 or Fura molecular probes can be used. As an example, intracellular $Ca^{2+}$ imaging is obtained using a confocal system (e.g. Bio-Rad Laser Scanning Confocal System interfaced to an Olympus IX-70 inverted microscope equipped with an Olympus 60_1.4 NA oil objective). Fluo-3 or other can be used as fluorescent $Ca^{2+}$ sensitive dye excited by the 488-nm beam of an argon-ion laser, and the fluorescence is acquired at wavelengths of 515 nm in the line scan mode of the confocal system at rate of 2 or 6 ms per scan. The magnitude of fluorescent signals is quantified in terms of F/F0, where F0 is baseline fluorescence. Assuming that the basal cytosolic $[Ca^{2+}]$ is 100 nmol/L and a Kd for Fluo-3 $Ca^{2+}$ binding of 1.1 µmol/L,[17] the theoretical maximum for F/F0 is 12. $Ca^{2+}$ spark parameters are quantified with a detection/analysis computer algorithm.

RyR2 R4496C myocytes electrical abnormalities are also detected by single cell electrophysiology measurements. These experiments are performed using patch-clamp technique. Using patch electrodes, membrane currents can be measured in voltage clamp mode while action potential can be measured in current-clamp mode.

Typically, laminin-coated dishes containing isolated ventricular myocytes are placed on the stage of an inverted microscope in a standard Tyrode solution and kept at physiological temperature. Transmembrane potentials and currents are recorded in whole cell current mode (e.g. using a MultiClamp 700B amplifier, Axon Instruments) using patch electrodes both in current clamp and in voltage clamp modes. Data are digitized and analyzed with a dedicated software. According to a preferred embodiment, myocytes are electrically stimulated by intracellular current injection through patch electrodes using depolarizing pulses i.e. with duration of 3 ms and amplitude of 1.5-2.5 nA. In this setup several stimulation protocols, known by the skilled artisan, can be applied to study arrhythmogenic mechanisms due to the presence of the RyR2-R4496C mutation in comparison with wild type cells. Typically: trains of several (i.e. 20) pulses followed by few (i.e. 5) seconds pause are delivered at 1-5 Hz in control conditions and few (5) minutes after exposure to isoproterenol (30 nM) to activate the adrenoreceptors. Electrical activity of the cell is studied in term of action potential (current-clamp). Furthermore, transient inward current ($I_{Ti}$) may be elicited by repeated trains of 14, 100-ms voltage-clamp steps from −80 to 50 mV. Similar electrophysiological studies and stimulation protocols can also be carried out in myocardial tissue preparations using microelectrodes.

Additional assays for determining the RyR2 or mutant RyR2 channel activity are selected in the group consisting of:

(i) recording of single or multiple RyR2 channel openings in lipid bilayers using art-recognized procedures as described e.g. in[18, 19];

(ii) determination of calcium release from SR vesicles using art-recognized procedures, such as, for example, those described by[20, 21].

In assaying for enhanced cardiac RyR2 channel activity, an enhanced channel open probability (Po) is detected. The higher channel opening probability leads to enhanced calcium efflux or release from the SR, and enhances cardiac contractility and excitability (i.e. arrhythmogenic). Vascular tone and cardiac contractility may be also measured and recorded in the in vivo animal model.

In contrast, inhibitors of cardiac mutant RyR2 channel activity will decrease the channel open probability, reduce calcium release from the SR, and reduce cardiac contractility. Vascular tone may also be reduced and this can be recorded. Additional methods of determining modified cardiac RyR2 channel activity are not excluded and are comprised within the present invention.

Accordingly, a further aspect of the invention provides a method for identifying a drug candidate able to abolish, reduce or prevent the effect of the R4496C mutation on cells isolated from the transgenic animal comprising: (i) incubating an amount of a potential drug candidate or a homologue, analogue or derivative thereof that modulates the mutant cardiac RyR2 channel activity under conditions suitable for channel activity; (ii) incubating the same drug candidate in control cells or in cells carrying a wild type cardiac RyR2 under conditions appropriate for wild type channel activity to be modulated by said drug candidate or a homologue, analogue or derivative thereof and determining the activity of the channel; and (iii) comparing the activity at (i) and (ii) by statistical analysis. Cardiac RyR2 channel activities comprise, as a non exhaustive list, the following measurable RyR2 channel activities: $Ca^{2+}$ flux, ryanodine binding to the receptor, RyR2 substrate phosphorilation, cell contractility.

According to the above embodiments the methods disclosed for isolated cardiomyocytes are useful in: (i) identifying antiarrhythmic candidate compounds, (ii) identifying drugs interfering negatively with the RyR2 mutation, in particular with the R4496C, or with the human homologous mutation, (iii) identifying candidate drug such as agonists and antagonists of the cardiac mutant RyR2 calcium channel; (iv) identifying mechanism underlying the arrhythmogenic event at the cellular level, (v) screening test compounds interfering with the arrhythmogenic event, such as agonists and antagonists of the cardiac mutant RyR2 calcium channel cardiac mutant RyR2 calcium channel.

The in vitro assays may be performed on cells isolated from transgenic animals, as well as on tissue preparations or extracts, such as microsomal preparations of cardiac muscle. In particular rapid, high throughput screening to identify drug candidates can be carried out incubating for example microsomal preparations of cardiac muscle or of isolated cardiomyocytes expressing the mutant RyR2 transgene. The molecules being screened may be isotopically labelled so as to permit ready detection of interaction.

Cardiac mutant RyR2 cells isolated from the transgenic animals can optionally be infected, transfected or transformed in vitro with vectors carrying additional transgenes, for example reporter genes, to achieve a rapid identification of the cell response.

Screening of multiple candidate compounds such as libraries of compounds, may comprise High Throughput methods. According to this embodiment the compounds may be attached to a plurality of polymeric pins or supports. The invention further comprise any detection method able to determine RyR2 functions in vitro on isolated cells (preferably cardiomyocytes), tissues or organs.

Method of Use of the Transgenic Animal.

The RyR2 transgenic animals are essential tools in the understanding of the molecular basis of CPVT and arrhythmias. The RyR2 transgenic animal are also essential tools in drug screening for evaluating the therapeutic potential of a putative drug candidate. In any of these embodiments, the in vivo measurements of cardiac activity before and after test conditions, comprise at least one of the following measure: continuous ECG monitoring or echocardiography after or during the induction of cardiac stress. Cardiac stress is typically induced with exercise (on a treadmill, by swimming etc) preferably in combination with beta adrenergic stimulation and/or with administration of pharmacological agents or "stressors", able to modulate the activity (as described above) of the autonomic nervous system and/or the intracellular $Ca^{2+}$ handling (such as $Ca^{2+}$ antagonists, modulators of RyR2 activities, or binders to RyR2 such as calstabin, or modulators of other RyR2 regulating peptides).

In addition any measurement known in the art and able to detect cardiac function or dysfunction and applicable to in vivo animals, is comprised within the methods of the invention.

As an example, measure of cardiac functions may also comprise determination of cardiac contractility as described in[22, 23]. For any in vitro or in vivo measure, however, those skilled in the art are aware that a potential drug candidate shows an effect which is dependent on the drug concentration. The parameter(s) on which a potential drug candidate may be active are selected from the group consisting of: contractility as assessed by dP/dtmax, left ventricular systolic pressure, and heart rate. Ventricular fibrillation or other cardiac arrhythmia can also be determined to quantify negative side-effects of the potential drug candidate (test compound) or of drugs negatively interacting with RyR2 mutation.

The transgenic mouse of the invention represents also a valuable model to determine arrhythmogenic compounds (i.e. drugs interacting w/a mutant RyR2 and which may represent a risk for silent carriers of a RyR2 mutation). Interaction of a putative arrhythmogenic compound is measured in vivo or in vitro after administration of a RyR2 activator such as caffeine, adrenaline, isoproterenol, phenilephrine, beta and alpha receptors agonists in general, and 4-Chloro-m-cresol (4-CmC), their homologues, analogues or derivatives thereof.

The RyR2 transgenic mouse is also essential in screening and evaluating compounds. A test compound is typically administered to transgenic mice and cardiac parameters are evaluated before and after administration. The response of treated transgenic animals is compared to the one of untreated transgenic animals and of wild type treated and untreated animals by statistical methods.

As said above, experimental protocols for screening putative drug candidates typically combine stress inducing conditions such as exercise stress or pharmacological RyR2 modulation in RyR2 mutant transgenic rodents with administration of potential drug candidates (test compound/s), in combination with other pharmacological agents or adrenergic compounds (isoproterenol, epinephrine, other adrenergic agonists, caffeine).

Methods of screening potential class or classes of drug candidates, i.e. able to prevent or treat RyR2 dependent arrhythmias in humans and/or animals or able to ameliorate the symptoms of these pathologic conditions, comprise the treatment of the transgenic rodents with molecules of the following classes of drugs:

heart rate-lowering agents;
potential RyR2 binding agents, such as K201 (formerly called JTV519),
selective blocker of the Na+/Ca++ exchanger, such as SEA0400,
beta blockers and/or alpha+beta blockers, and the measure of the cardiac function by the above defined parameters, in the above defined stress condition and compared to the one of control animals. Suitable controls may comprise untreated transgenic animals or wild type treated and untreated animals. The comparison is carried out by statistical methods.

A drug candidate is defined as a molecule which in a "effective amount" diminish or reverse the progression of a parameter selected as the most suitable "dysfunction marker".

It is also defined for the purpose of the present invention, that the term drug or class of drug, embraces all homologues, analogues and derivatives of a candidate compound.

Administration of drug candidates in vivo is performed by oral and/or parenteral route or by intraperitoneal, intravenous, spray, intradermal, or intracardiac routes. The response and the parameters measured for the transgenic rodents are compared to the ones of wild type animals or of control animals with statistical methods (i.e. one way ANOVA, Bonferroni test). The ability of the screened compounds to prevent arrhythmias or to diminish the sensibility of the transgenic rodents according to the present invention to arrhythmogenic stimuli, i.e. stimuli which typically induces arrhythmias in R4496C transgenic rodents, is directly related to their therapeutic value as antiarrhythmic compounds for use in human therapy.

Data obtained from cell based assays and animal studies can be used in formulating a range of dosage of the drug candidate for use in humans. The dosage of the drug candidate, homologue, analogue, or derivative, lies preferably within a range of concentrations that, following administration by a particular route, produce a circulating concentration consistent with the ED50 and having little or no toxicity.

For purposes of this aspect of the invention, beneficial or desired pre-clinical results in the transgenic rodents include, but are not limited to, alleviation of symptoms, diminishment of extent of disease, stabilization of the disease state, delay or slowing of disease progression, amelioration or palliation of the disease state, reduction of the sensibility to arrhythmogenic stimuli, and remission (whether to partial or total), whether detectable or undetectable. "Treatment" also includes prolonging survival as compared to the expected survival of a subject not receiving treatment. As used herein, the term "treatment" includes prophylaxis.

As a summary, according to the above embodiments the transgenic animal model carrying the RyR2 mutation R4496C, is useful in: (i) identifying antiarrhythmic candidate compounds, (ii) identifying drugs interfering negatively with the RyR2 mutation, in particular with the R4496C, or with the human homologous mutation, (iii) identifying candidate drug such as agonists and antagonists of the cardiac mutant RyR2 calcium channel; (iv) identifying mechanism underlying the arrhythmogenic event in vivo, (v) screening test compounds interfering with the arrhythmogenic event and potentially preventing sudden death in a human subject suffering from CPVT and/or in treating or preventing arrhythmias related to RyR2 mutations.

It is intended that the research activities disclosed in the present invention can be based either on cell-based assays or on animal based assays, including for example the in vivo characterisation on the animal level as well as measurements on single cardiomyocytes (cellular $Ca^{2+}$ signalling; patch clamp: action potentials and ion currents).

A further embodiment of the transgenic rodents or of the isolated cells according to the invention, is their use as in vivo or in vitro model for the gene therapy of RyR2 mediated arrhythmias, by treatment with viral vectors or antisense technology (siRNA).

According to still another embodiment, the transgenic mice of the invention, are useful in cross-breeding experiments with mice harbouring abnormalities in other proteins controlling intracellular calcium handling in order to gather further pathophysiological insights.

The invention will be better described in the following non-limiting experimental examples.

Example 1

Generation of Conditional Knock-in of RyR2 in Mouse Model

We amplified by PCR a 900 bp segment encompassing exons 94 and 95 of the RyR2 gene using exonic primers identified on mouse RyR2 cDNA (GenBank Acc. N° NM_023868). This fragment was used as a probe to screen a 129SV/J lambda mouse genomic library (Stratagene): 800.000 phages were screened and two positive plaques were isolated. Through Southern blot hybridization we identified one 3850 bp fragment (BamHI) and one 3500 bp fragment (XbaI) that were cloned into pBluescript (Stratagene) and sequenced to define the genomic structure of is the mouse RyR2 gene. Site-direct mutagenesis (Quick-Change™, Stratagene) was performed to introduce the point mutation R4496C in exon 94 in the BamHI fragment.

The targeting vector pFrIt1 (Gene bank: AY268481) contained a PGK-Neo gene flanked by Frt sites used for the selection with G418 (Geneticin), a HSV-TK cassette (outside the region of homology) for the selection with gancyclovir and two LoxP sites for the conditional knock-in. The 0.6 kb PstI/ApaI blunted fragment containing exon 94 with the R4496C mutation isolated from pBluescript-3850 was inserted into the BamHI blunted site of pFrIt1 between LoxP sites. The 2.3 kb SalI fragment, containing the intronic region between exon 93 and exon 94 isolated from pBluescript-3850, was cloned into the SalI site of pFrIt1. The 1.2 XhoI fragment containing the exon 95 isolated from pBluescript-3500, was cloned into the XhoI site of pFrIt1. The targeting vector linearized with KpnI was transfected into the TVB2 embryonic stem (ES) cells by electroporation (FIG. 1). TVB2 is a ES cell line derived from 129SV mouse with the same genetic background. Cells were plated in 100 mm dishes and were cultured for 48 hours. Positive and negative selections were carried out using Geneticin (G418) and gancyclovir respectively. 200 clones were obtained and analyzed for the homologous recombination into the mouse RyR2 gene by PCR using the vector primer PF-1951+(5'-CCGGTGGAT-GTGGAATGTGTGCG-3') and exon primer P-96R (5'-GAT-CACAAGTCTGTCCCACTGGCC-3'). One positive clone was isolated and confirmed by Southern blot using an external probe to the target sequence of homology. The positive clone was injected into the blastocysts of C57BL/6 mice and chimaeric animals were obtained (Core Facility for Conditional Mutagenesis, Dibit-San Raffaele Scientific Institute, Milan). Chimaeric male mice were bred to C57BL/6 female mice to establish a hybrid line. In fact germline transmission has generated$^{RyR}2^+$/RyR$^{R4496C\text{-}neo}$ mice with genetic background 129SV/J from ES cells and C57BL/6 from blastocysts. The genotypes from the F1 and F2 generations were determined by PCR on DNA from tail biopsy specimens (DNeasy Tissue Kit Qiagen). RyR2$^+$/RyR$^{R4496c\text{-}neo}$ male mice were bred to female mice that expressed FIp recombinase to remove the selectable marker (neo). The genotypes from F1 generation without neo were determined by PCR on DNA from tail biopsy specimens (DNeasy Tissue Kit Qiagen).

Animals were maintained and bred at the Charles River Laboratories in Calco, Italy, and transferred to the Maugeri Foundation for characterization of the phenotype. Animals were maintained and studied according to the protocols approved by the Animal Care and Use facility at the Maugeri Foundation.

Example 2

Development and Pathology of WT and RyR2$^+$/RyR$^{R4496C}$ Mice

No difference between the WT vs RyR2$^+$/RyR$^{R4496C}$ animals was present in the duration of the pregnancy, delivery, size and survival of litters, development and behaviour. Young adult mice of both genders entered the experimental protocol: no difference in the weight between WT and RyR2$^+$/RyR$^{R4496C}$ mice was observed (mean weight WT 25.6±3.6 gr; RyR2$^+$/RyR$^{R4496C}$ 27.3±4.9 gr; p=0.189).

Figure 2:
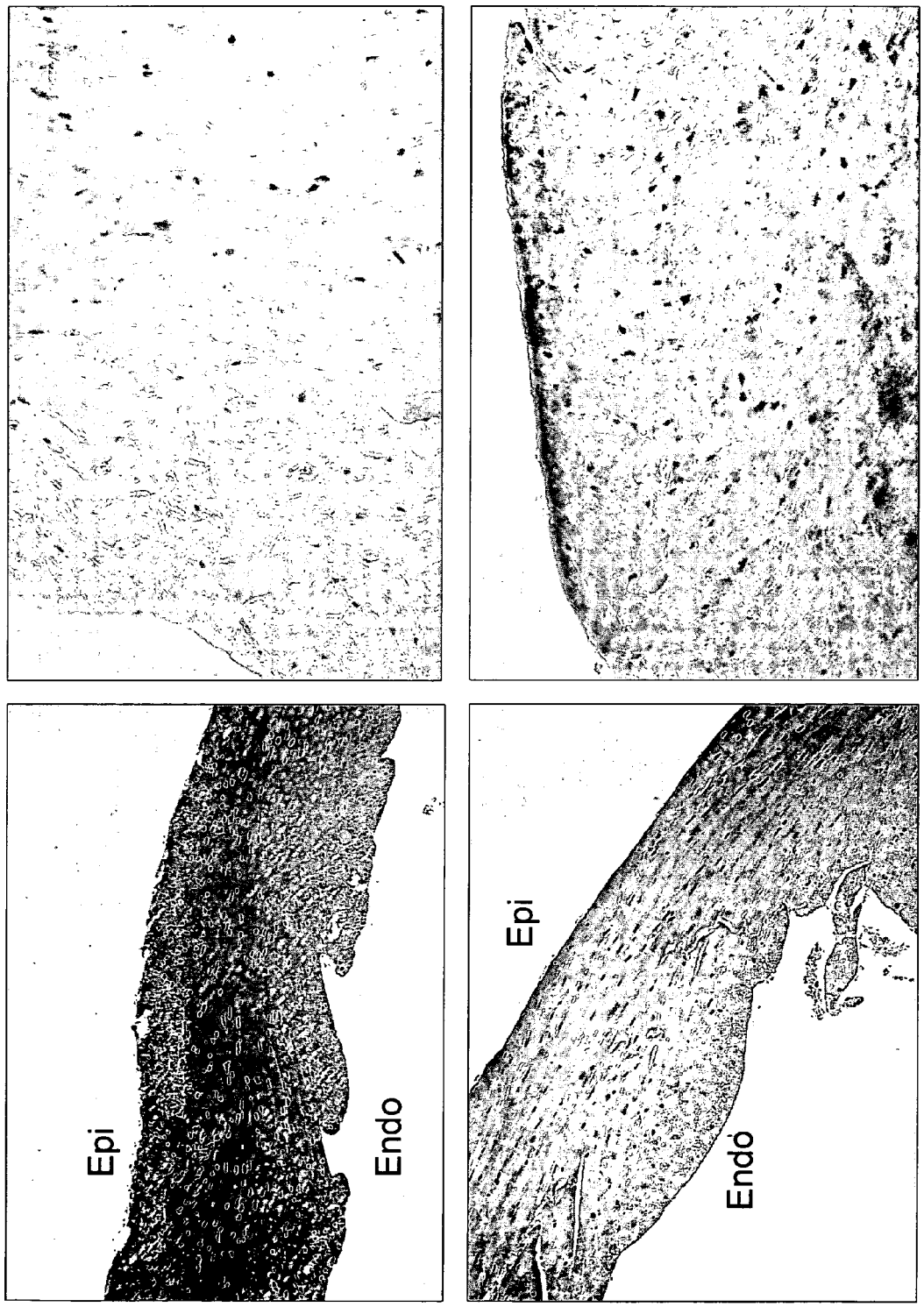
FIG. 2. Panel A: Hematoxylin-Eosin stain (250×) of a section of the right ventricle of a wild type mouse. Panel B: Trichromic Masson stain (400×) of a section of the right ventricle of a wild type mouse. Panel C: Hematoxylin-Eosin stain (250×) of a section of the right ventricle of a $RyR^{R4496C}$ mouse. Panel D: Trichromic Masson stain (400×) of a section of the right ventricle of a $RyR^{R4496C}$ mouse. Endo=endocardium; Epi=epicardium.

Gross inspection did not show any macroscopic alteration of the heart and vessels. Histological examination was carried out on hearts of eight months old mice (WT n=2 and RyR2$^+$/RyR$^{R4496C}$ n=3) excised, stored in 10% formalin, serially sectioned. The sections were fixed with 10% formalin and stained with hematoxylin-eosin and/or Masson stain and analyzed with routine light microscopy. No tissue abnormalities, no fibrous-fatty infiltration was observed, no signs suggestive of right ventricular cardiomyopathy were identified in the mutant mice and in the controls (FIG. 2).

Example 3

Phenotype Characterization Under Exercise or Adrenergic Activation Testing

Measures, Statistical Analysis and Definitions.

Statistical analysis was performed using the SPSS statistical package (v. 12.01). Parametric tests were used to compare normally distributed variables (unpaired t-test and ANOVA with Bonferroni correction for multiple comparisons). Cross tabulations with chi-square or Fisher's exact test were used as appropriate for categorical variables. Data are expressed as mean±standard deviation.

Arrhythmias were defined as follows: non sustained ventricular tachycardia (VTns) was defined as a series of 4 to 10 consecutive repetitive ventricular ectopic beats (VEBs), sustained VT (VTsust) was defined as a run of >10 consecutive VEBs, ventricular fibrillation (VF) was defined as a VTsust degenerating into ventricular fibrillation leading to sudden death.

ECG radiotelemetry monitors (Data Sciences International) were implanted intraabdominally under general anaesthesia (Avertin 0.025 mg/kg). Body temperature was maintained at 37° C. by use of a thermally controlled heating pad (Harvard Apparatus). ECG was continuously monitored starting 48 h after surgery. After 72 hours of recovery from surgery phenotype characterization was performed.

One group (Group 1) of animals exercised on a treadmill until exhaustion. The animals were then injected with epinephrine 2 mg/kg i.p. (WT n=12, RyR2$^+$/RyR$^{R4496C}$ n=14). A second group of animals (Group 2) was injected with epinephrine (2 mg/kg ip) and caffeine (120 mg/kg i.p.) (WT, n=8, RyR2$^+$/RyR$^{R4496C}$, n=7). ECG monitoring was performed continuously during both exercise and drug testing protocols. Five additional RyR2$^+$/RyR$^{R4496C}$ animals were treated for 24 hours with propranolol i.p. (2 mg/Kg) every 12 hours before being exposed to the epinephrine and caffeine protocol.

Continuous ECG monitoring revealed the absence of spontaneous ventricular arrhythmias both in WT and RyR2$^+$/RyR$^{R4496C}$ mice. Interestingly the RyR2$^+$/RyR$^{R4496C}$, at variance with CPVT patients, did not manifest supraventricular arrhythmias during EG monitoring.

Figure 3:
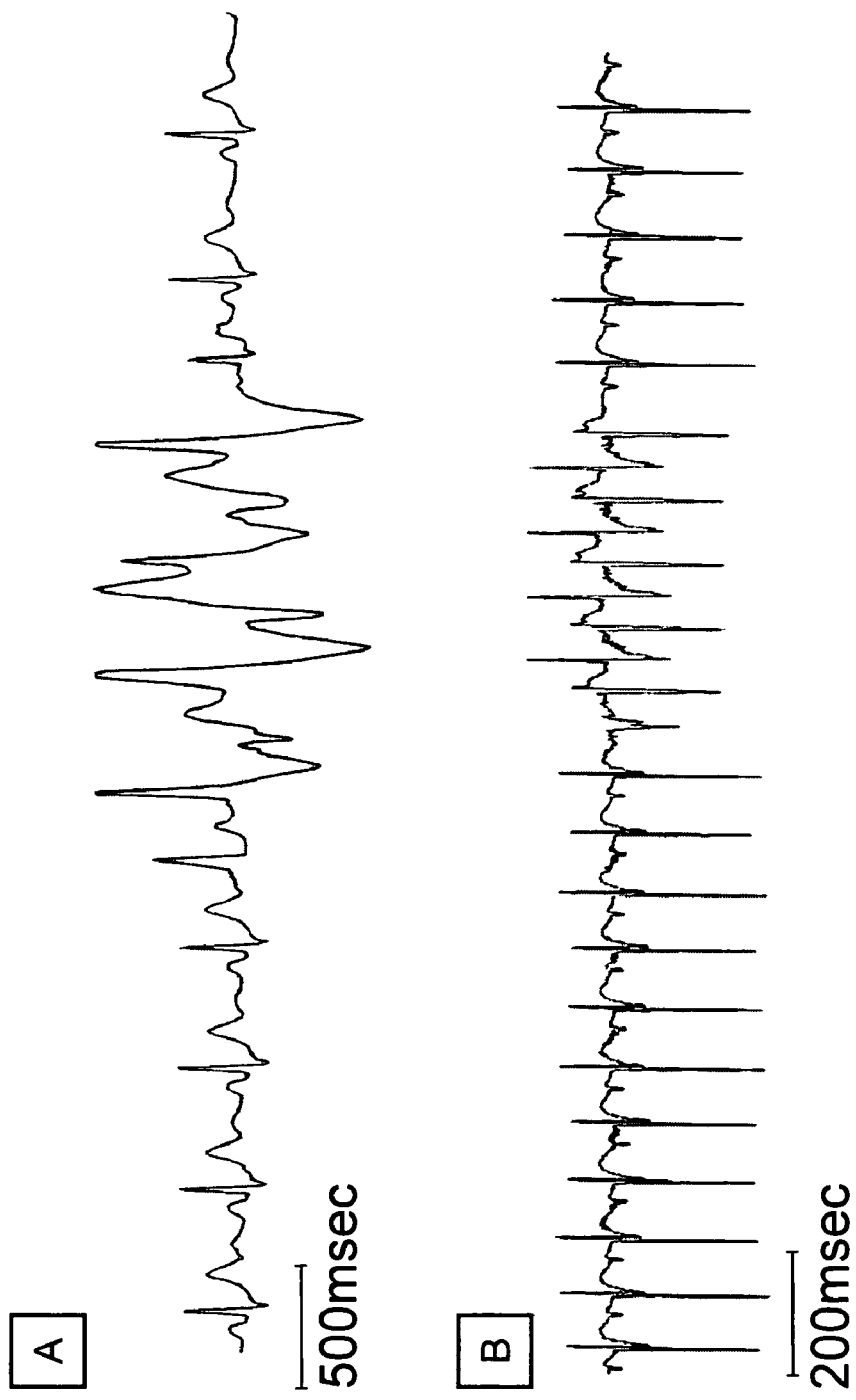
FIG. 3. Panel A: ECG recording of nonsustained bidirectional VT in a CPVT patient. Panel B: ECG recording of a nonsustained bidirectional VT in a $RyR2^+/RyR^{R4496C}$ mouse. msec=milliseconds.

Group 1 (26 mice: 12 WT and 14 RyR2$^+$/RyR$^{R4496C}$) underwent exercise stress testing followed by epinephrine administration. The QT interval and RR interval of the WT and of the mutant mice did not present significant differences (Table I). None of the 12 WT mice developed repetitive ventricular arrhythmias while 5/14 RyR2$^+$/RyR$^{R4496C}$ mice developed VTsus (n=3) or VTns (n=2; FIG. 3 Panel B) (WT vs RyR2$^+$/RyR$^{R4496C}$; p=0.02; Table I).

Group 2 (21 mice: 8 WT, 8 RyR2$^+$/RyR$^{R4496C}$ and 5 RyR2$^+$/RyR$^{R4496C}$ pre-treated with beta-blockers) received epinephrine and caffeine i.p. The QT interval (measured using the tangent method[24] and RR interval of the WT and of the mutant mice did not present significant differences (Table I), the RR interval was significantly prolonged in the RyR2$^+$/RyR$^{R4496C}$ animals pretreated with betablockers (Table I).

Figure 4:
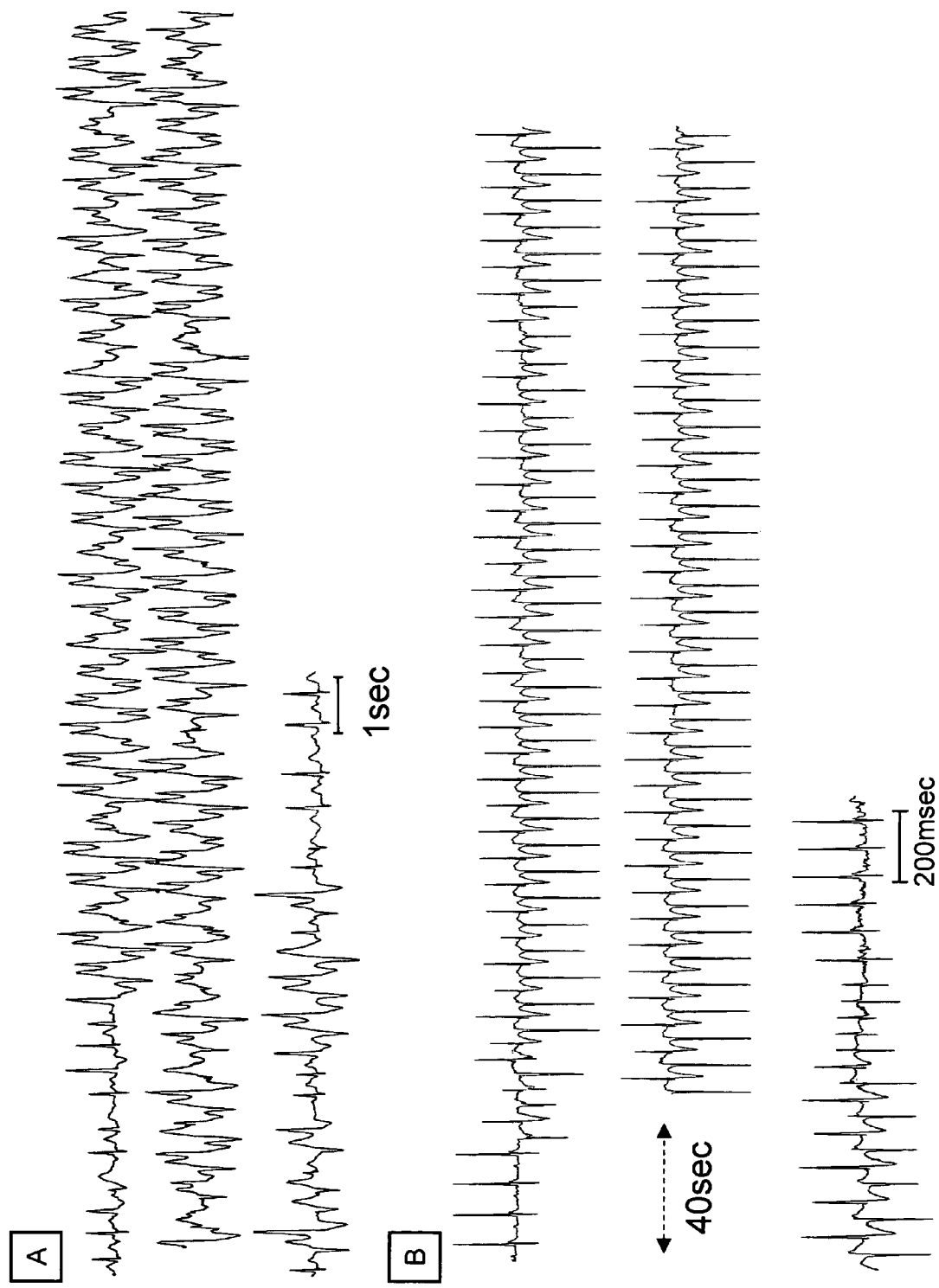
FIG. 4. Panel A: ECG recording of sustained and self terminating bidirectional VT in a CPVT patient. Panel B: ECG recording of a sustained and self terminating bidirectional VT in a $RyR2^+/RyR^{R4496C}$ mouse. msec=milliseconds; sec=seconds.
Figure 5:
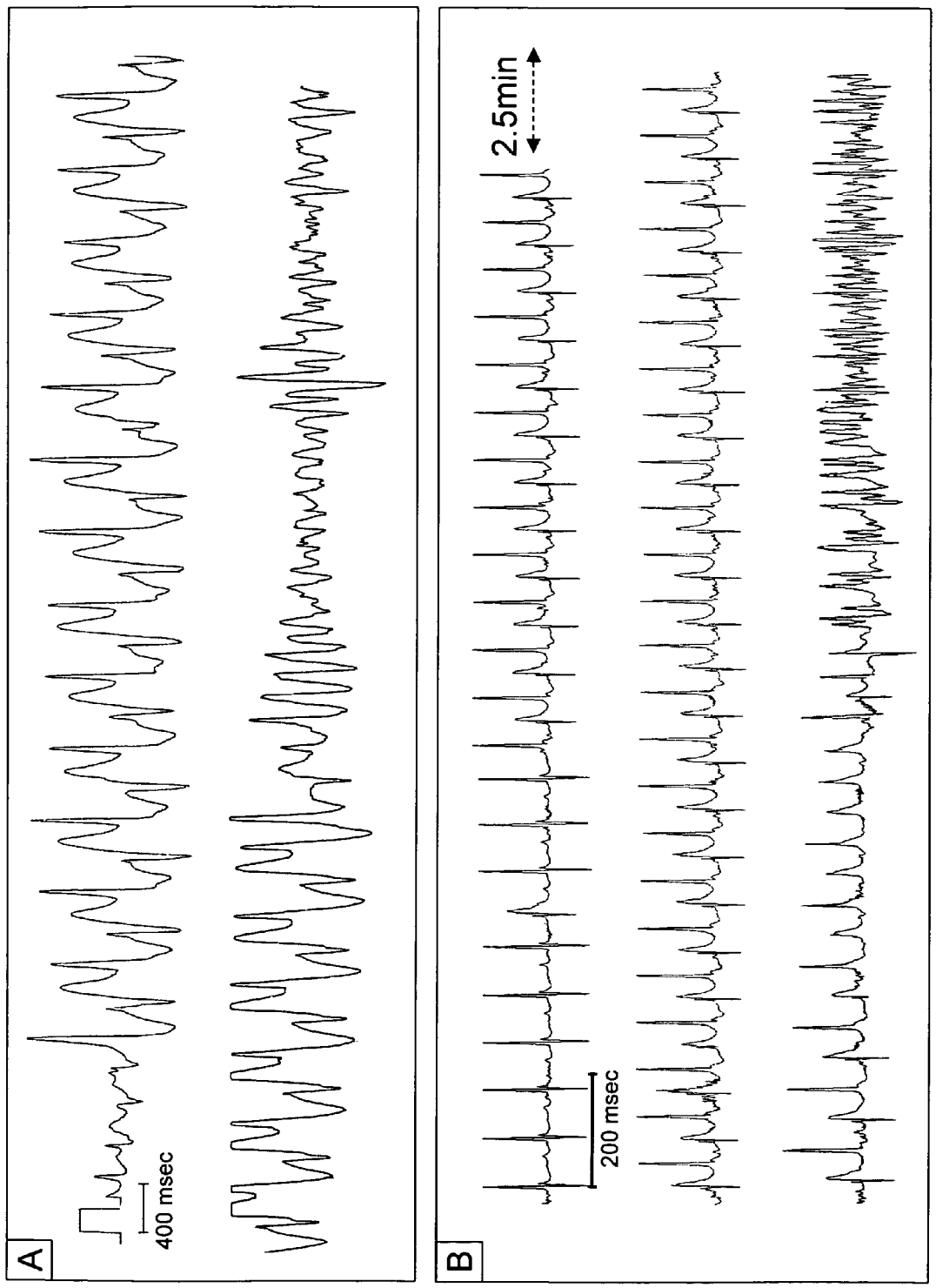
FIG. 5. Panel A: ECG recording of a bidirectional VT degenerating into VF in a CPVT patient. Panel B: ECG recording of a of a bidirectional VT degenerating into VF in a $RyR2^+/RyR^{R4496C}$ mouse. msec=milliseconds; min=minutes.

The epinephrine and caffeine test induced more severe is arrhythmias than the exercise protocol. Two WT mice developed VTns 6 had no arrhythmias; thus none of the WT animals experienced sustained cardiac arrhythmias. Among the RyR2$^+$/RyR$^{R4496C}$ mice 4/8 or 50% developed sustained arrhythmias (VTsust n=2; FIG. 4 panel B and VF n=2; FIG. 5 panel B p=0.02 versus WT; Table I).

It is remarkable that VT in the RyR2$^+$/RyR$^{R4496C}$ mice had the typical bidirectional morphology that is considered the most distinguishing characteristics of CPVT patients (FIGS. 3, 4 and 5 Panel A).

Figure 6:
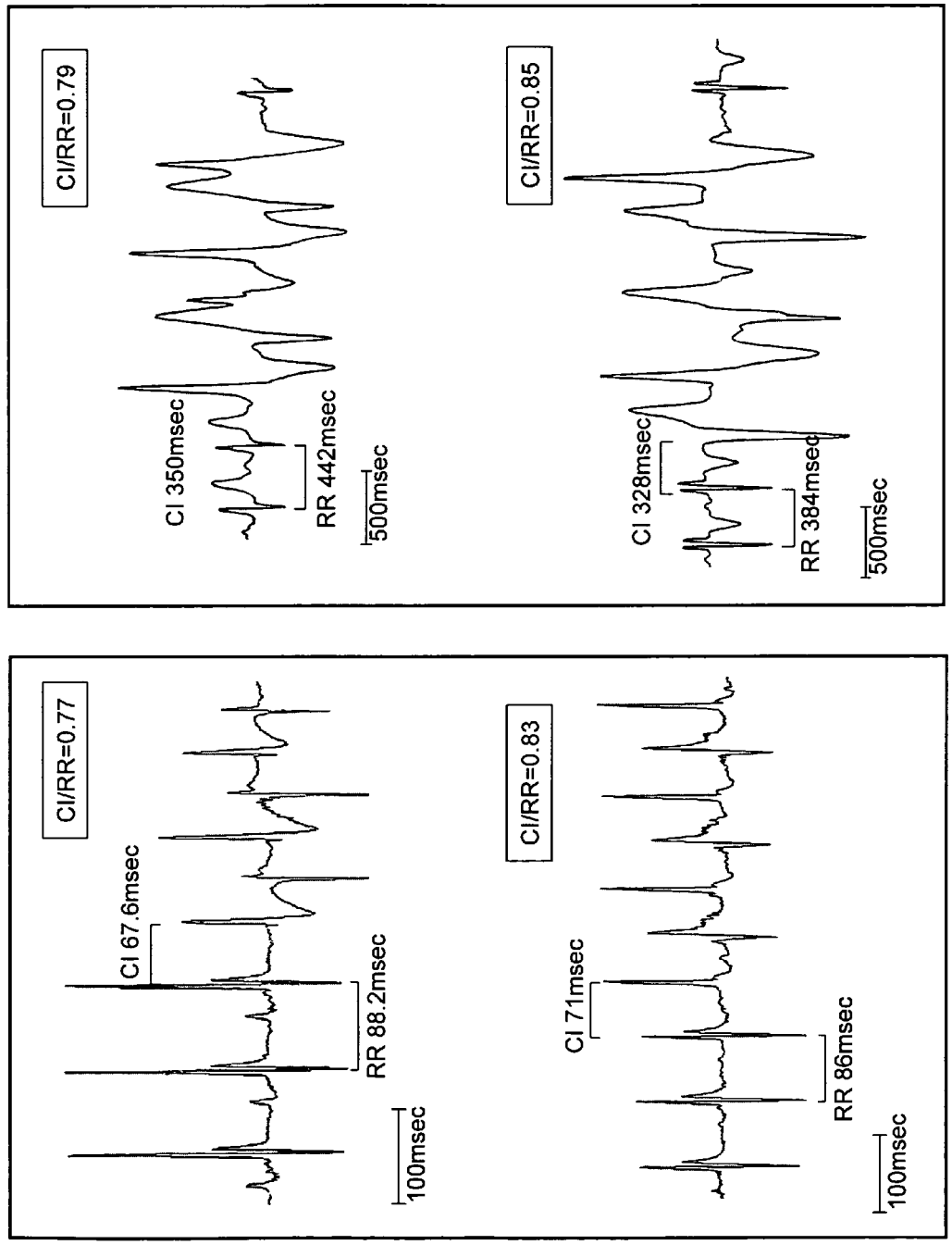
FIG. 6. Panel A: Coupling interval of the initiating beat of polymorphic ventricular tachycardia in CPVT patients. Panel B: Coupling interval of the initiating beat of polymorphic ventricular tachycardia in $RyR2^+/RyR^{R4496C}$ mice CI=Coupling Interval; interval in msec between an extrasystolic beat and the preceding sinus beat; RR=interval between two consecutive sinus beats; CI/RR=ratio between the coupling interval of an extrasystolic beat and the preceding RR interval. msec=milliseconds.

The coupling interval of the beats initiating VTs was only slightly shorter than the preceding RR interval (Table I), R-on T phenomenon was never observed: these features are similar to those observed in CPVT patients (FIG. 6). Panel B of FIGS. 3, 4 and 5 show examples of a non sustained VT, of a sustained VT that spontaneously terminates and of a sustained VT degenerating into VF respectively. In panel A of the same figures similar arrhythmias recorded in CPVT patients are shown. These data clearly show how our invention closely matches the clinical manifestation of CPVT, and specifically the typical beat-to-beat QRS polarity alternans, the so-called bi-directional ventricular tachycardia that may lead to ventricular fibrillation and cardiac arrest. Therefore this transgenic model has a relevant clinical pathophysiological relevance to the understanding of CPVT arrhythmias and other arrhythmias related to abnormal intracellular calcium handling.

Example 4

Analysis of the Allele-Specific Transcription of the RyR2 Gene

At the end of the experimental protocols animals were anesthetized and sacrificed by cervical dislocation and the heart was immediately excised. Total mRNA was extracted using a RNAEasy Fibrous Tissue Midi Kit (Qiagen). cDNA was generated using random examer from 2.5 µg of mRNA using a Thermoscript RT-PCR system (Invitrogen). PCR fragments encompassing the mutation were to amplified from cDNAs using p93F and p94R primers (5'CCACATCGC-TATGGGGAGCCGAAG 3' (seq IDNO4) and 5' CGAAG-GCAACAAACAAGGCCAGC 3' (seqIDNO5)) using Taq Platinum (Invitrogen). PCR products were purified with a QIAquick gel Extraction Kit (Qiagen) and quantified with an UV/visible spectrophotometer. Single nucleotide primer extension was performed with a SnaPshot Multiplex Kit (Applied Biosystems) as suggested by the manufacturer in a 10 µL reaction using 0.36 pmol of the template and 0.2 µM primer (seqIDNO6) 5' CAGCATTCTCATGTTG-TAAAAGTTGC 3' (HPSF purified, MWG-Biotech). The reactions were run on a ABI PRISM 310 Genetic Analyzer and analyzed using the Gene Scan software (Applied Biosystems).

The relative quantification of allele-specific expression of the RyR2 gene in the heart of heterozygous mice under Group 1 or Group 2 treatment conditions, was carried out by single nucleotide primer extension method[25]. Total mRNA was available for 24/27 RyR2$^+$/RyR$^{R4496C}$ mice from Group 1 and Group 2. 10/24 of the mice developed either VTns or VTs while 14 had no arrhythmias. The WT-to-R4496C mRNA ratio was similar in the two groups (R4496C-mRNA=0.66±0.14 in the heart of the mice without arrhythmias and 0.67±0.02 in the mice with arrhythmias; NS). The relative quantification of allele-specific transcription of the RyR2 gene in the heterozygous mice was carried out in order to investigate if the variability in the pattern of arrhythmias elicited in response to exercise and/or pharmacological challenges correlates with the allele specific transcription of RyR2. The relative transcription of WT and mutant mRNA in the heart of the RyR2$^+$/RyR$^{R4496C}$ mice showed that the mutant mRNA was slightly underrepresented as compared to the wild type mRNA, but no differences in the levels of the mutant mRNA were present between the animals that developed arrhythmias and those that remained asymptomatic throughout the provocative tests. It is concluded that the severity of the arrhythmias is not related to the allele-specific transcription of RyR2.

Example 5

In Vivo Drug-Testing

Five RyR2$^+$/RyR$^{R4496C}$ mice were treated with propranolol to evaluate if antiadrenergic compounds could prevent induction of arrhythmias. After drug administration we observed a prolongation of RR interval from 94.5±13 to 118±13 msec beats per minute (p<0.001). Interestingly the effect of betablockers on heart rate in RyR2$^+$/RyR$^{R4496C}$ mice was not different from the effect on WT mice (mean prolongation or RR interval was as follows RyR2$^+$/RyR$^{R4496C}$ mice 23.62±0.14 msec vs WT mice 22.92±3.6 msec p=0.69; the percentage of RR is change after betablockers (Δ%=ΔRR*100/RR baseline) was RyR2$^+$/RyR$^{R4496C}$ mice 25±3% versus WT mice 27±5% p=0.52). Despite pretreatment with betablockers, the administration of caffeine and epinephrine elicited VTsust in 2 and VF in 2 (sustained arrhythmias in 4 mice); only one mouse had no arrhythmias (p=0.56; i.e. non significant versus RyR2+/RyR$^{R4496C}$ mice).

Example 6

Cross-Breeding

Transgenic animals will be used in cross-breeding experiments to:
1) assess the effect of the modulation of RyR2 expression level on the susceptibility to cardiac arrhythmias. This may comprise cross-breed heterozygous RyR2-R4497C mice in order to create a homozygous RyR2 defective mouse;
2) study how the wild type and mutant RyR2 channels are modulated in vivo by CaMKII delta phosphorylation. The RyR2-R4497C is cross-bred with a CaMKII delta overexpressing mouse (calcium/calmodulin-dependent protein kinase II). The possibility of will give the opportunity of dissecting out the pathophysiology of Calcium-induced Calcium release mechanism and related cardiac arrhythmias. More importantly these studies will open the possibility to identify a novel pharmacological target to modulate Ca2+ release in disease states through interference with the RyR2 phosphorylation pathway. These studies will help in identifying "modifiers" potentially triggering RyR2-mediated arrhythmias;
3) identify the effects of RyR2 stabilizers. In order to determine the feasibility of this therapeutic intervention, crossbreeding with FKBP12.6 (calstabin) overexpressing mouse are planned.

These approaches will help in clarifying the importance of potential therapeutic approaches or evaluating substances or events triggering RyR2-mediated arrhythmias.

Example 7

Gene Expression Profile

The availability of an animal model such as the one of the present invention opens the possibility to perform a detailed study of the gene expression profile in CPVT. The microarray technology can be applied to compare the gene expression profile of the heart of wild type mice with that of RyR2 R4496C mice. We will compare WT and RyR2 R4496C hearts from littermates wild type. In a second step we will compare gene expression profile of animals with a severe arrhythmic phenotype versus animals with low susceptibility to cardiac arrhythmias. Subsequent comparison of the data obtained in the two sets of experiments will allow the identification of the orthologous genes, whose expression should be altered as a direct consequence of CPVT. (.methods for studying the gene expression profile are described for example in[26].

After having identified a panel of genes differentially expressed in mice with R4496C RyR2 and in R4496C mice with arrhythmias versus R4496C mice resistant to arrhythmias, we will confirm the results at mRNA level with Northern blotting and at the protein level using Western blotting and co-immunoprecipitation in cardiac myocytes derived from the TG animals. Finally, Gene Ontology analysis will provide the way to examine the interplay between the proteins controlling the intracellular Ca2+ and to identify novel therapeutic targets.

CONCLUSION

Our results provide the previously missing demonstration that the presence of the R4496C mutation predisposes the murine heart to the development of bidirectional and polymorphic VT and to ventricular fibrillation upon administration of caffeine and of adrenergic agonists. Combined with the evidence provided by in vitro characterization of the same RyR2 mutant[5-8] it seems plausible to suggest that arrhythmias in the RyR2$^+$/RyR$^{R4496C}$ mice are caused by enhanced calcium release from the sarcoplasmic reticulum through the defective RyR2 channels.

None of the functional studies performed so far proved that the presence of RyR2$^{R4496C}$ channels is able to induce sustained ectopic activity leading to VT and VF upon exposure to the RyR-agonist caffeine or during adrenergic stimulation. The present study fills that gap by showing that polymorphic and even bidirectional VT may be elicited in the RyR2$^+$/RyR$^{R4496C}$ mice under conditions that strictly resemble those eliciting cardiac arrhythmias in CPVT patients. Consistent with the incomplete penetrance of the CPVT phenotype in humans, not all RyR2$^+$/RyR$^{R4496C}$ mice developed arrhythmias. The cause for incomplete penetrance is today the most puzzling aspect of inherited arrhythmogenic diseases and no satisfactory explanation has been provided to account for the major differences in the clinical manifestations observed among affected patients, even when they are members of the same family. Both genetic and environmental factors[27] have been advocated to account for this variability but a robust hypothesis supported by experimental data is missing.

Patients affected by the R4497C mutation have a malignant form of the disease. Cardiac arrest occurred in 7/13 (53%) carriers of the mutation and in 4 patients it was a lethal event. Furthermore VT or VF occurred in 5 patients also during beta-blocker therapy suggesting that the protection afforded by these agents may not be sufficient to prevent life-threatening events in CPVT[2]. Treatment with propranolol was not effective in preventing arrhythmias in RyR2$^+$/RyR$^{R4496C}$ mice thus confirming the observation made in humans. This model will allow to investigate why the R4497C mutation in humans is particularly resistant to antiadrenergic interventions. There is also strong rational to support the idea that this mouse model will be useful to gather insights on the pathophysiology of the other RyR2-CPVT mutations.

In conclusion, the phenotype of the murine model that has been developed presents remarkable similarity with the clinical manifestations of patients carriers of the R4497C mutations in terms of arrhythmias morphology, severity and the incomplete response to beta blockers. This knock-in rodent model will allow to clarify several yet uncertain aspects of CPVT and may provide a valuable tool for investigating novel treatments for CPVT patients.

CITED REFERENCES

1 Leenhardt, A., Lucet, V., Denjoy, I. et al. Catecholaminergic polymorphic ventricular tachycardia in children. A 7-year follow-up of 21 patients. Circulation 1995; 91:1512-1519.

2 Priori, S. G., Napolitano, C., Memmi, M. et al. Clinical and molecular characterization of patients with catecholaminergic polymorphic ventricular tachycardia. Circulation 2002; 106:69-74.

3 Swan, H., Piippo, K., Viitasalo, M. et al. Arrhythmic disorder mapped to chromosome 1q42-q43 causes malignant polymorphic ventricular tachycardia in structurally normal hearts. J Am Coll Cardiol 1999; 34:2035-2042.

4 Priori, S. G., Napolitano, C., Tiso, N. et al. Mutations in the Cardiac Ryanodine Receptor Gene (hRyR2) Underlie Catecholaminergic Polymorphic Ventricular Tachycardia. Circulation 2001; 103:196-200.

5. Jiang, D., Xiao, B., Yang, D. et al. RyR2 mutations linked to ventricular tachycardia and sudden death reduce the threshold for store-overload-induced Ca2+ release (SOICR). Proc Natl Acad Sci USA 2004; 101:13062-13067.

6 Jiang, D., Xiao, B., Zhang, L., Chen, S. R. Enhanced basal activity of a cardiac Ca2+ release channel (ryanodine receptor) mutant associated with ventricular tachycardia and sudden death. Circ Res 2002; 91:218-225.

7 George, Christopher H., Higgs, Gemma V., Lai, F. Anthony. Ryanodine Receptor Mutations Associated With Stress-Induced Ventricular Tachycardia Mediate Increased Calcium Release in Stimulated Cardiomyocytes. Circ Res 2003; 93:531-540.

8 Wehrens, X. H., Lehnart, S. E., Huang, F. et al. FKBP12.6 deficiency and defective calcium release channel (ryanodine receptor) function linked to exercise-induced sudden cardiac death. Cell 2003; 113:829-840.

9 Laitinen, P. J., Brown, K. M., Piippo, K. et al. Mutations of the cardiac ryanodine receptor (RyR2) gene in familial polymorphic ventricular tachycardia. Circulation 2001; 103:485-490.

10. Benkusky, N. A., Farrell, E. F., Valdivia, H. H. Ryanodine receptor channelopathies. Biochem Biophys Res Commun 2004; 322:1280-1285.

11 Sambrook J, Fritsch E F, Maniatis T. Molecular Cloning. A Laboratory manual. Second ed. New York: Cold Spring Harbor Laboratory Press, 1989.

12 Rodriguez, C. I., Buchholz, F., Galloway, J. et al. High-efficiency deleter mice show that FLPe is an alternative to Cre-loxP. Nat Genet 2000; 25:139-140.
13 Karreman, C. New positive/negative selectable markers for mammalian cells on the basis of Blasticidin deaminase-thymidine kinase fusions. Nucleic Acids Res 1998; 26:2508-2510.
14 Cerrone, Marina, Colombi, Barbara, Santoro, Massimo et al. Bidirectional Ventricular Tachycardia and Fibrillation Elicited in a Knock-In Mouse Model Carrier of a Mutation in the Cardiac Ryanodine Receptor (RyR2). Circ Res 2005; 96:e77-e82.
15. Sambrano, G. R., Fraser, I., Han, H. et al. Navigating the signalling network in mouse cardiac myocytes. Nature 2002; 420:712-714.
16 Viatchenko-Karpinski, Serge, Terentyev, Dmitry, Gyorke, Inna et al. Abnormal Calcium Signaling and Sudden Cardiac Death Associated With Mutation of Calsequestrin. Circ Res 2004; 94:471-477.
17 Harkins, A. B., Kurebayashi, N., Baylor, S. M. Resting myoplasmic free calcium in frog skeletal muscle fibers estimated with fluo-3. Biophys J 1993; 65:865-881.
18 Zahradnikova, A., Zahradnik, I., Gyorke, I., Gyorke, S. Rapid activation of the cardiac ryanodine receptor by sub-millisecond calcium stimuli. J Gen Physiol 1999; 114:787-798.
19 Gyorke, I., Gyorke, S. Regulation of the cardiac ryanodine receptor channel by luminal Ca2+ involves luminal Ca2+ sensing sites. Biophys J 1998; 75:2801-2810.
20 el Hayek, R., Yano, M., Antoniu, B. et al. Altered E-C coupling in triads isolated from malignant hyperthermia-susceptible porcine muscle. Am J Physiol 1995; 268: C1381-C1386.
21 Ahern, G. P., Junankar, P. R., Pace, S. M. et al. Effects of ivermectin and midecamycin on ryanodine receptors and the Ca2+-ATPase in sarcoplasmic reticulum of rabbit and rat skeletal muscle. J Physiol 1999; 514:313-326.
22 Tesi, C., Colomo, F., Nencini, S., Piroddi, N., Poggesi, C. Modulation by substrate concentration of maximal shortening velocity and isometric force in single myofibrils from frog and rabbit fast skeletal muscle. J Physiol 1999; 516:847-853.
23 Colomo, F., Piroddi, N., Poggesi, C., te, Kronnie G., Tesi, C. Active and is passive forces of isolated myofibrils from cardiac and fast skeletal muscle of the frog. J Physiol 1997; 500:535-548.
24 Lande, G., Demolombe, S., Bammert, A. et al. Transgenic mice overexpressing human KvLQT1 dominant-negative isoform. Part II: Pharmacological profile. Cardiovasc Res 2001; 50:328-334.
25. Tournier, I., Raux, G., Di Fiore, F. et al. Analysis of the allele-specific expression of the mismatch repair gene MLH1 using a simple DHPLC-Based Method. Hum Mutat 2004; 23:379-384.
26 Volinia, S., Evangelisti, R., Francioso, F. et al. GOAL: automated Gene Ontology analysis of expression profiles. Nucleic Acids Res 2004; 32:W492-W499.
27 Priori, S. G. Inherited Arrhythmogenic Diseases: The Complexity Beyond Monogenic Disorders. Circ Res 2004; 94:140-145.

TABLE I

|  | N | Baseline QT | Baseline RR | VTns | VTsust & VF | All VT/VF |
|---|---|---|---|---|---|---|
| GROUP 1 | | | | | | |
| WT | 12 | 24 + 2^ | 91 + 10° | 0 | 0 | 0 |
| RyR2$^+$/RyR$^{R4496C}$ | 14 | 25 + 2^ | 90 + 12° | 2 | 3 | 5* |
| GROUP 2 | | | | | | |
| WT | 8 | 24 + 0.2§ | 91 + 9* | 2 | 0 | 2 |
| RyR2$^+$/RyR$^{R4496C}$ | 8 | 24 + 0.1§ | 83 + 10* | 0 | 4** | 4 |
| Beta blockade in RyR2$^+$/RyR$^{R4496C}$ | 5 | 23 + 0.2§ | 121 + 23* | 0 | 4 | 4 |

RyR2$^+$/RyR$^{R4496C}$ = Heterozygous mice carriers of the R4496C mutation;

WT = Wild Type mice;

VTns = Non sustained Ventricular Tachycardia;

VTsust = sustained VT;

VF = Ventricular Fibrillation;

All VT/VF = sum of animals experiencing VTns or VTsust or VF.

For definition of arrhythmias see the methods.

*P = 0.02 RyR2$^+$/RyR$^{R4496C}$ versus WT,

**P = 0.02 RyR2$^+$/RyR$^{R4496C}$ versus WT

Group 1 Baseline QT interval Independent sample t-test: ^p = 0.886 Baselines RR interval Independent sample t-test: °p = 0.929;

Group 2: Baseline RR One way ANOVA *p < 0.0001; post hoc tests (Bonferroni): WT vs RyR2$^+$/RyR$^{R4496C}$ p = 0.949; WT vs Beta blockade in RyR2$^+$/RyR$^{R4496C}$ p = 0.001; RyR2$^+$/RyR$^{R4496C}$ vs Beta blockade in RyR2$^+$/RyR$^{R4496C}$ p = 0.0001

Baseline QT interval One way ANOVA § P = 0.966

We claim:

1. A transgenic mouse model for Catecholaminergic Polymorphic Ventricular Tachycardia (CPVT) on a genetic basis carrying an R4496C mutation in the cardiac Ryanodine receptor (RyR2) gene in a heterozygous form, wherein sustained ectopic activity leading to bidirectional Ventricular Tachycardia (VT) and Ventricular Fibrillation (VF) is obtained by exposure of the mouse to a RyR-agonist (caffeine) or during adrenergic stimulation and wherein said transgenic mouse model further exhibits the following characteristics:
   adrenergically mediated arrhythmogenesis;
   normal electrocardiogram at baseline;
   lack of fatty fibrous infiltration in the heart;
   absence of extra-cardiac abnormalities;
   incomplete response to beta blocker therapy; and
   incomplete penetrance.

2. The transgenic mouse according to claim 1 with a C57B1 genetic background.

3. The transgenic mouse according to claim 1 wherein such mutation is introduced by a replacement vector carrying a mutated exon 94.

4. The transgenic mouse according to claim 3 wherein said mutated exon 94 comprises SEQ ID NO:2.

5. The transgenic mouse according to claim 4 wherein the genomic replacement of exon 94 with the mutated exon 94 on the replacement vector occurs because of the presence of a 5' and of a 3' arms of homology comprising SEQ ID NO:1 and SEQ ID NO:3.

6. The transgenic mouse according to claim 1 which is a conditional mutant.

7. A cell or tissue isolated from the transgenic mouse according to claim 1.

8. The cell according to claim 7 which is a cardiomyocyte.

9. A method to identify an antiarrhythmic activity of a test compound which comprises:
   i) incubating an isolated cell or tissue according to claim 7 in suitable growth conditions and in the presence of suitable concentrations of a test compound or of a plurality of test compounds;
   ii) measuring at least one of the following activities: $Ca^{2+}$ fluxes, action potential and transmembrane currents, ryanodine binding to the receptor, cell contractility, and RyR2 mediated substrate phosphorylation;
   iii) analyzing the data measured in ii);
   iv) determining if the candidate test compound has any effect on cardiomyocyte activity.

10. The method according to claim 9 wherein in step ii) action potential is measured by patch electrodes both in current clamp and in voltage clamp modes.

11. The method according to claim 9 wherein in step ii) transmembrane currents are measured by a single cell electrophysiology technique.

12. A method to determine the therapeutic or a prophylactic activity of a test compound in CPVT, in arrhythmias or in a RyR2 mediated sudden death syndrome comprising:
   i) administering said test compound to the transgenic mouse according to claim 1,
   ii) measuring a cardiac functionality parameter and/or heart morphology and/or blood pressure;
   iii) comparing the measure in ii) to the measure obtained in suitable control mice, by statistical analysis.

13. The method according to claim 12 wherein said cardiac functionality parameter is selected from the group consisting of: arrhythmias, heart rate trends, heart rate variability, QT interval and T wave assessments, baseline QT interval, RR interval, and RR variability.

14. The method according to claim 13 wherein said parameter is measured by ECG and/or continuous monitoring ECG.

15. The method according to claim 12 wherein in ii) the heart morphology is determined by echocardiography or by NMR.

16. The method according to claim 12 wherein before administration in i) the transgenic mouse is placed under cardiac stress conditions.

17. The method according to claim 16 wherein said cardiac stress conditions are induced by physical exercise and/or treatment with a RyR2 activator selected from the group consisting of: caffeine, adrenaline, isoproterenol, phenilephrine, beta and alpha receptor agonists, 4-Chloro-m-cresol (4-CmC), and homologues, analogues, derivatives or salts thereof.

18. A method for identifying the molecular basis and pathophysiology of CPVT wherein the transgenic mouse of claim 1 is bred to a wild type or transgenic mouse.

19. A replacement vector comprising a mutated RyR2 gene exon 94, wherein said mutation leads to a R4496C mutation in the RyR2 receptor for the preparation of the transgenic mouse according to claim 1.

20. The replacement vector according to claim 19 wherein said mutation in exon 94 of the RyR2 gene is a C→T mutation in the codon corresponding to nt 387-389 of SEQ ID NO:2.

\* \* \* \* \*

UNITED STATES PATENT AND TRADEMARK OFFICE
CERTIFICATE OF CORRECTION

| | |
|---|---|
| PATENT NO. | : 7,741,529 B1 |
| APPLICATION NO. | : 11/429167 |
| DATED | : June 22, 2010 |
| INVENTOR(S) | : Priori et al. |

It is certified that error appears in the above-identified patent and that said Letters Patent is hereby corrected as shown below:

On the Title Page, under Item (54) (Title), replace "USE" with --USES--.

On the Title Page, under Item (56) OTHER PUBLICATIONS, in Kappell et al., replace "Kappell" with --Kappel--.

On the Title Page, under Item (56) OTHER PUBLICATIONS, in Sigmund et al., replace "Arteroscler." with --Arterioscler.--.

Column 3, Line 59, replace "recording of a of a bidirectional" with --recording of a bidirectional--.

Column 4, Line 59, replace "FIp" with --Flp--.

Column 8, Line 4, replace "substrate phosphorilation" with --substrate phosphorylation--.

Column 10, Line 17, replace "whether to partial" with --whether partial--.

Column 11, Line 1, replace "structure of is the mouse" with --structure of the mouse--.

Column 11, Line 5, replace "pFrIt1" with --pFrlt1--.

Column 11, Line 12, replace "pFrIt1" with --pFrlt1--.

Column 11, Line 15, replace "pFrIt1" with --pFrlt1--.

Column 11, Line 17, replace "pFrIt1" with --pFrlt1--.

Column 11, Line 36, replace "$^{RyR}2^+/RyR^{R4496C\text{-}neo}$" with --$RyR2^+/RyR^{R4496C\text{-}neo}$--.

Column 11, Line 40, replace "$RyR2^+/RyR^{R4496c\text{-}neo}$" with --$RyR2^+/RyR^{R4496C\text{-}neo}$--.

Signed and Sealed this
First Day of May, 2012

David J. Kappos
*Director of the United States Patent and Trademark Office*

CERTIFICATE OF CORRECTION (continued)
U.S. Pat. No. 7,741,529 B1

Column 13, Line 1, replace "more severe is" with --more severe--.

Column 14, Line 29, replace "RR is change" with --RR change--.

Column 17, Line 3, replace "Cre-IoxP" with --Cre-loxP--.

UNITED STATES PATENT AND TRADEMARK OFFICE
CERTIFICATE OF CORRECTION

| | |
|---|---|
| PATENT NO. | : 7,741,529 B1 |
| APPLICATION NO. | : 11/429167 |
| DATED | : June 22, 2010 |
| INVENTOR(S) | : Priori et al. |

It is certified that error appears in the above-identified patent and that said Letters Patent is hereby corrected as shown below:

On the Title Page, under Item (54) and at Column 1, line 4, (Title), replace "USE" with --USES--.

On the Title Page, under Item (56) OTHER PUBLICATIONS, in Kappell et al., replace "Kappell" with --Kappel--.

On the Title Page, under Item (56) OTHER PUBLICATIONS, in Sigmund et al., replace "Arteroscler." with --Arterioscler.--.

Column 3, Line 59, replace "recording of a of a bidirectional" with --recording of a bidirectional--.

Column 4, Line 59, replace "FIp" with --Flp--.

Column 8, Line 4, replace "substrate phosphorilation" with --substrate phosphorylation--.

Column 10, Line 17, replace "whether to partial" with --whether partial--.

Column 11, Line 1, replace "structure of is the mouse" with --structure of the mouse--.

Column 11, Line 5, replace "pFrIt1" with --pFrlt1--.

Column 11, Line 12, replace "pFrIt1" with --pFrlt1--.

Column 11, Line 15, replace "pFrIt1" with --pFrlt1--.

Column 11, Line 17, replace "pFrIt1" with --pFrlt1--.

Column 11, Line 36, replace "$^{RyR}2^{+}/RyR^{R4496C\text{-}neo}$" with --$RyR2^{+}/RyR^{R4496C\text{-}neo}$--.

This certificate supersedes the Certificate of Correction issued May 1, 2012.

Signed and Sealed this
Twenty-ninth Day of May, 2012

David J. Kappos
*Director of the United States Patent and Trademark Office*

CERTIFICATE OF CORRECTION (continued)
U.S. Pat. No. 7,741,529 B1

Column 11, Line 40, replace "RyR2$^+$/RyR$^{R4496c\text{-}neo}$" with --RyR2$^+$/RyR$^{R4496C\text{-}neo}$--.

Column 13, Line 1, replace "more severe is" with --more severe--.

Column 14, Line 29, replace "RR is change" with --RR change--.

Column 17, Line 3, replace "Cre-IoxP" with --Cre-loxP--.